United States Patent
Henkin et al.

[11] Patent Number: 5,932,545
[45] Date of Patent: Aug. 3, 1999

[54] ANTIANGIOGENIC DRUG TO TREAT CANCER, ARTHRITIS AND RETINOPATHY

[75] Inventors: Jack Henkin, Highland Park; Noel P. Bouck, Oak Park; David W. Dawson, Chicago; Andrew J. Schneider, Gurnee, all of Ill.

[73] Assignee: Abbott Laboratories, Abbott Park, Ill.

[21] Appl. No.: 09/039,682

[22] Filed: Mar. 16, 1998

Related U.S. Application Data

[60] Provisional application No. 60/041,155, Mar. 17, 1997.
[51] Int. Cl.$^6$ .................................................. A61K 38/00
[52] U.S. Cl. ........................... 514/13; 530/326; 530/327; 530/328; 514/13; 514/14; 514/15; 514/16
[58] Field of Search .................................... 530/326, 327, 530/328; 514/13, 14, 15, 16

[56] References Cited

FOREIGN PATENT DOCUMENTS

| 0443404 | 2/1991 | European Pat. Off. .......... C07K 7/00 |
| 9316716 | 9/1993 | WIPO .............................. A61K 37/02 |
| 9505191 | 2/1995 | WIPO . |

OTHER PUBLICATIONS

Journal of Peptide Research, vol. 50, No. 3 (Sep. 1997), pp. 210–221, Guo et al., "Antiproliferative and Antitumor Activities of D–Reverse Peptides Derived from the Second Type–1 Repeat of Thrombospondin–1".

*Primary Examiner*—Avis M. Davenport
*Attorney, Agent, or Firm*—Gregory W. Steele

[57] ABSTRACT

Peptides having the formula:

T-Gly-Val-D-Ile-Thr-Arg-Ile-U,

V-Gly-D-Val-Ile-D-Thr-D-Arg-D-Ile-W,

X-D-Arg-D-Ile-D-Arg-D-Thr-Ile-D-Val-Y, and

Z-Gly-Val-Ile-Thr-Arg-Ile-U wherein T is absent or is selected from N-protecting group and a polypeptide of up to 12 amino acid residues optionally terminated with a N-protecting group; U is selected from Arg and Arg-NR$^1$R$^2$ wherein R$^1$ and R$^2$ are independently selected from hydrogen and alkyl of one to four carbon atoms; V is absent or a N-protecting group; W is selected from D-Arg and D-Arg-NR$^1$R$^2$; X is absent or a N-protecting group; Y is selected from Gly and Gly-NR$^1$R$^2$; and Z is 1–12 amino acid residues optionally terminated with a N-protecting group wherein at least one of the amino acid residues is a D-amino acid residue inhibit angiogenesis and are useful in the treatment of disease states such as cancer, arthritis, macular degeneration and diabetic retinopathyin which angiogenesis plays a role.

34 Claims, No Drawings

ANTIANGIOGENIC DRUG TO TREAT CANCER, ARTHRITIS AND RETINOPATHY

This application claims benefit of Provisional application Ser. No. 60/041,155 filed Mar. 17, 1997.

TECHNICAL FIELD

The present invention relates to compounds useful for treating pathological states which arise or are exacerbated by angiogenesis. More particularly, the invention relates to certain peptides which inhibit angiogenesis, to pharmaceutical compositions comprising these compounds and to a method inhibiting angiogenesis.

BACKGROUND OF THE INVENTION

Angiogenesis is the fundamental process by which new blood vessels are formed and is essential to a variety of normal body activities (such as reproduction, development and wound repair). Although the process is not completely understood, it is believed to involve a complex interplay of molecules which both stimulate and inhibit the growth of endothelial cells, the primary cells of the capillary blood vessels. Under normal conditions, these molecules appear to maintain the microvasculature in a quiescent state (i.e. one of no capillary growth) for prolonged periods which may last for as long as weeks or in some cases, decades. When necessary however (such as during wound repair), these same cells can undergo rapid proliferation and turnover within a 5 day period. (Folkman, J. and Shing, Y., *The Journal of Biological Chemistry*, 267(16): 10931–10934, and Folkman, J. and Klagsbrun, M., *Science*, 235: 442–447 (1987)).

Although angiogenesis is a highly regulated process under normal conditions, many diseases (characterized as "angiogenic diseases") are driven by persistent unregulated angiogenesis. Otherwise stated, unregulated angiogenesis may either cause a particular disease directly or exasperate an existing pathological condition. For example, ocular neovacularization has been implicated as the most common cause of blindness and dominates approximately 20 eye diseases. In certain existing conditions such as arthritis, newly formed capillary blood vessels invade the joints and destroy cartilage. In diabetes, new capillaries formed in the retina invade the vitreous, bleed, and cause blindness. Growth and metastasis of solid tumors are also angiogenesis-dependent (Folkman, J., *Cancer Research*, 46: 467–473 (1986), Folkman, J., *Journal of the National Cancer Institute*, 82: 4–6 (1989)). It has been shown for example that tumors which enlarge to greater than 2 mm, must obtain their own blood supply and do so by inducing the growth of new capillary blood vessels. Once these new blood vessels become embedded in the tumor, they provide a means for tumor cells to enter the circulation and metastasize to distant sites, such as liver, lung or bone (Weidner, N., et al., *The New England Journal of Medicine*, 324(1): 1–8 (1991)).

Thrombospondin-1 (TSP1, MW 450,000) is a large modular matrix protein that inhibits neovascularization in vivo (Good, et al., *Proc. Natl. Acad Sci. USA.*, 87, 6624 (1980)). The majority of the antiangiogenic activity of TSP1 resides in the central 70-kD stalk region. Synthetic peptides were prepared which mimic sequences found in the properdin-like repeat region 1 of the central stalk region of TSP1 molecule. One of these peptides, the so-called MalII, is a 19-mer of formula Ser-Pro-Trp-Ser-Ser-Ala-Ser-Val-Thr-Ala-Gly-Asp-Gly-Val-Ile-Thr-Arg-Ile-Arg (Tolsma, et al., *J. Cell Biol.*, 122, 497 (1993)). The MalII peptide blocked neovascularization in vivo in the rat cornea and inhibited the migration of cultured endothelial cells with an $ED_{50}$ of about 1 $\mu$M.

Although several angiogenesis inhibitors are currently under development for use in treating angiogenic diseases (Gasparini, G. and Harris, A. L., *J Clin Oncol* 13(3): 765–782, (1995)), there are disadvantages associated with several of these compounds. For example, suramin is a potent angiogenesis inhibitor, but causes (at doses required to reach antitumor activity) severe systemic toxicity in humans. Other compounds, such as retinoids, interferons and antiestrogens are safe for human use but have only a weak anti-angiogenic effect. Still other compounds may be difficult or costly to make. Short peptides are relatively simple to make and represent a cost effective method of treating disease states in which angiogenesis plays a role and in designing targeted inhibitors of angiogenesis.

SUMMARY OF THE INVENTION

In its principle embodiment, the present invention provides a peptide, or a pharmaceutically acceptable salt thereof selected from the group consisting of T-Gly-Val-D-Ile-Thr-Arg-Ile-U, I, and Z-Gly-Val-Ile-Thr-Arg-Ile-U

IV wherein T is absent or is selected from a N-protecting group and a polypeptide of up to 12 amino acid residues optionally terminating with a N-protecting group; U is selected from Arg and Arg-$NR^1R^2$ wherein $R^1$ and $R^2$ are independently selected from hydrogen and alkyl of one to four carbon atoms; and Z is 1–12 amino acid residues optionally terminated with a N-protecting group wherein at least one of the amino acid residues is a D-amino acid residue.

Preferred compounds of the present invention have the formula T-Gly-Val-D-Ile-Thr-Arg-Ile-U, wherein T is absent or is selected from N-protecting group and a polypeptide of up to 12 amino acid residues optionally capped with N-protecting group and U is selected from Arg and Arg-$NR^1R^2$.

More preferred compounds are those of formula T-Gly-Val-D-Ile-Thr-Arg-Ile-U wherein T is absent or acetyl and U is selected from the group consisting of Arg, Arg-$NH_2$ and Arg-$NHCH_2CH_3$.

In another embodiment, the present invention provides retro isomers of the above peptides, or retro-inverso isomers of the above peptides, or pharmaceutically acceptable salts thereof. Exemplary retro and retro-inverso isomers are selected from the group consisting of

| V-D-Gly-D-Val-Ile-D-Thr-D-Arg-D-Ile-W and | II |
|---|---|
| X-D-Arg-D-Ile-D-Arg-D-Thr-Ile-D-Val-Y, | III | wherein V is absent or a N-protecting group; W is selected from D-Arg and D-Arg-$NR^1R^2$; X is absent or a N-protecting group; and Y is selected from Gly and Gly-$NR^1R^2$.

In another embodiment, the present invention provides a composition for treating a patient in need of anti-angiogenesis therapy comprising a peptide defined above in combination with a pharmaceutically acceptable carrier.

In yet another embodiment, the present invention provides a method for treating a patient in need of anti-angiogenesis therapy comprising administering to the patient a therapeutically effective amount of a peptide as defined above.

In yet another embodiment, the present invention provides a composition for the treatment of a disease selected from the group consisting of cancer, arthritis, psoriasis, angiogenesis of the eye associated with with infection or surgical intervention, macular degeneration and diabetic retinopathy comprising a peptide as defined above in combination with a pharmaceutically acceptable carrier.

In yet another embodiment, the present invention provides a treatment for a disease selected from the group consisting of cancer, arthritis, macular degeneration and diabetic retinopathy comprising administering to the patient a therapeutically effective amount of a peptide as defined above.

In yet another embodiment, the present invention provides a method of isolating the TSP-1 receptor from endothelial cells comprising binding a peptide of Formulas I and IV to the receptor, isolating the peptide receptor complex and purifying the receptor.

DETAILED DESCRIPTION

The term "alkyl" refers to a monovalent group derived from a straight or branched chain saturated hydrocarbon by the removal of a single hydrogen atom. Alkyl groups are exemplified by methyl, ethyl, n- and iso-propyl, n-, sec-, iso- and tert-butyl, and the like.

The term "N-protecting group", as used herein, refers to an easily removable group which is known in the art to protect an amino group against undesirable reaction during synthetic procedures and to be selectively removable. The use of N-protecting groups is well known in the art for protecting groups against undesirable reactions during a synthetic procedure and many such protecting groups are known, cf, for example, T. H. Greene and P. G. M. Wuts, Protective Groups in Organic Synthesis, 2nd edition, John Wiley & Sons, New York (1991). Examples of N-protecting groups include, but are not limited to, acyl groups including acetyl, trifluoroacetyl, acylisothiocyanate, aminocaproyl, benzoyl and the like, and acyloxy groups, including t-butyloxycarbonyl (BOC) and carbobenzyloxy, and the like.

The term "retro isomer", as used herein, refers to a peptide in which L and D amino acids of Formulas I and IV have been reversed, i.e., L amino acids have been substituted for D amino acids and D amino acids have been substituted for L amino acids. An exemplary retro isomer is of formula II. The term "retro isomers" include fragments of such isomers.

The term "retro-inverso isomer", as used herein, refers to a peptide in which (i) the L and D amino acids of Formulas I and IV have been reversed as in the retro isomer, and (ii) the sequence, when read from the N-terminus to the C-terminus, is reversed. An exemplary retro-inverso isomer is of formula III. The term "retro-inverso isomers" include fragments of such isomers.

By "pharmaceutically acceptable salt" it is meant those salts which are, within the scope of sound medical judgement, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describe pharmaceutically acceptable salts in detail in *J. Pharmaceutical Sciences,* 1977, 66: 1–19. The salts can be prepared in situ during the final isolation and purification of the compounds of the invention, or separately by reacting the free base function with a suitable organic acid. Representative acid addition salts include acetate, adipate, alginate, ascorbate, aspartate, benzenesulfonate, benzoate, bisulfate, borate, butyrate, camphorate, camphersulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts, and the like. Representative alkali or alkaline earth metal salts include sodium, lithium, potassium, calcium, magnesium, and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like.

As used herein, the term "pharmaceutically acceptable ester" refers to esters which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters includes formates, acetates, propionates, butyates, acrylates and ethylsuccinates.

The term "pharmaceutically acceptable prodrugs" as used herein refers to those prodrugs of the compounds of the present invention which are, within the scope of sound medical judgement, suitable for use in contact with with the tissues of humans and lower animals with undue toxicity, irritation, allergic response, and the like, commensurate with a reasonable benefit/risk ratio, and effective for their intended use, as well as the zwitterionic forms, where possible, of the compounds of the invention. The term "prodrug" refers to compounds that are rapidly transformed in vivo to yield the parent compound of the above formula, for example by hydrolysis in blood. A thorough discussion is provided in T. Higuchi and V. Stella, *Pro-drugs as Novel Delivery Systems,* Vol. 14 of the A. C. S. Symposium Series, and in Edward B. Roche, ed., *Bioreversible Carriers in Drug Design,* American Pharmaceutical Association and Pergamon Press, 1987, both of which are incorporated herein by reference.

Unless indicated otherwise by a "D" prefix, the stereochemistry of the α-carbon of the amino acids and aminoacyl residues in peptides described in this specification and the appended claims is the natural or "L" configuration. The Cahn-Ingold-Prelog "R" and "S" designations are used to specify the stereochemistry of chiral centers in certain of the acyl substituents at the N-terminus of the peptides of this invention. The designation "R,S" is meant to indicate a racemic mixture of the two enantiomeric forms. This nomenclature follows that described in R. S. Cahn, et al., *Angew. Chem. Int. Ed. Engl.,* 5, 385–415 (1966).

For the most part, the names on naturally-occurring and non-naturally occurring aminoacyl residues used herein follow the naming conventions suggested by the IUPAC Commission on the Nomenclature of Organic Chemistry and the IUPAC-IUB Commission on Biochemical Nomenclature as set out in "Nomenclature of α-Amino Acids (Recommendations, 1974)" Biochemistry, 14(2), (1975). To the extent that the names and abbreviations of amino acids and aminoacyl residues employed in this specification and appended claims differ from those suggestions, they will be made clear to the reader by the following.

It is well known in the art that modifications and changes can be made in the structure of a polypeptide without substantially altering the biological function of that peptide. For example, certain amino acids can be substituted for other amino acids in a given polypeptide without any appreciable loss of function. In making such changes, substitutions of like amino acid residues can be made on the basis of relative similarity of side-chain substituents, for example, their size, charge, hydrophobicity, hydrophilicity, and the like.

As detailed in United States Patent No. 4,554,101, incorporated herein by reference, the following hydrophilicity values have been assigned to amino acid residues: Arg (+3.0); Lys (+3.0); Asp (+3.0); Glu (+3.0); Ser (+0.3); Asn (+0.2); Gln (+0.2); Gly (0); Pro (–0.5); Thr (–0.4); Ala (–0.5); His (–0.5); Cys (–1.0); Met (–1.3); Val (–1.5); Leu (–1.8); Ile (–1.8); Tyr (–2.3); Phe (–2.5); and Trp (–3.4). It is understood that an amino acid residue can be substituted for another having a similar hydrophilicity value (e.g., within a value of plus or minus 2.0) and still obtain a biologically equivalent polypeptide.

In a similar manner, substitutions can be made on the basis of similarity in hydropathic index. Each amino acid residue has been assigned a hydropathic index on the basis of its hydrophobicity and charge characteristics. Those hydropathic index values are: Ile (+4.5); Val (+4.2); Leu (+3.8); Phe (+2.8); Cys (+2.5); Met (+1.9); Ala (+1.8); Gly (–0.4); Thr (–0.7); Ser (–0.8); Trp (–0.9); Tyr (–1.3); Pro (–1.6); His (–3.2); Glu (–3.5); Gln (–3.5); Asp (–3.5); Asn (–3.5); Lys (–3.9); and Arg (–4.5). In making a substitution based on the hydropathic index, a value of within plus or minus 2.0 is preferred.

Compounds contemplated as falling within the scope of the present invention include, but are not limited to:

Gly-Val-D-Ile-Thr-Arg-Ile-Arg,
Gly-Val-D-Ile-Thr-Arg-Ile-Arg-NH$_2$,
Gly-Val-D-Ile-Thr-Arg-Ile-Arg-NHCH$_2$CH$_3$,
Ac-Gly-Val-D-Ile-Thr-Arg-Ile-Arg,
Ac-Gly-Val-D-Ile-Thr-Arg-Ile-Arg-NH$_2$,
Ac-Gly-Val-D-Ile-Thr-Arg-Ile-Arg-NHCH$_2$CH$_3$,
Tyr-Gly-Val-D-Ile-Thr-Arg-Ile-Arg,
Tyr-Gly-Val-D-Ile-Thr-Arg-Ile-Arg-NH$_2$,
Tyr-Gly-Val-D-Ile-Thr-Arg-Ile-Arg-NHCH$_2$CH$_3$,
Ac-Tyr-Gly-Val-D-Ile-Thr-Arg-Ile-Arg,
Ac-Tyr-Gly-Val-D-Ile-Thr-Arg-Ile-Arg-NH$_2$,
Ac-Tyr-Gly-Val-D-Ile-Thr-Arg-Ile-Arg-NHCH$_2$CH$_3$,
D-Tyr-Gly-Val-D-Ile-Thr-Arg-Ile-Arg,
D-Tyr-Gly-Val-D-Ile-Thr-Arg-Ile-Arg-NH$_2$,
D-Tyr-Gly-Val-D-Ile-Thr-Arg-Ile-Arg-NHCH$_2$CH$_3$,
Ac-D-Tyr-Gly-Val-D-Ile-Thr-Arg-Ile-Arg,
Ac-D-Tyr-Gly-Val-D-Ile-Thr-Arg-Ile-Arg-NH$_2$,
Ac-D-Tyr-Gly-Val-D-Ile-Thr-Arg-Ile-Arg-NHCH$_2$CH$_3$,
Gly-Asp-Gly-Val-D-Ile-Thr-Arg-Ile-Arg,
Gly-Asp-Gly-Val-D-Ile-Thr-Arg-Ile-Arg-NH$_2$,
Gly-Asp-Gly-Val-D-Ile-Thr-Arg-Ile-Arg-NHCH$_2$CH$_3$,
Ac-Gly-Asp-Gly-Val-D-Ile-Thr-Arg-Ile-Arg,
Ac-Gly-Asp-Gly-Val-D-Ile-Thr-Arg-Ile-Arg-NH$_2$,
Ac-Gly-Asp-Gly-Val-D-Ile-Thr-Arg-Ile-Arg-NHCH$_2$CH$_3$,
Ser-Pro-Trp-Ser-Ser-Ala-Ser-Val-Thr-Ala-Gly-Asp-Gly-Val-D-Ile-Thr-Arg-Ile-Arg,
Ser-Pro-Trp-Ser-Ser-Ala-Ser-Val-Thr-Ala-Gly-Asp-Gly-Val-D-Ile-Thr-Arg-Ile-Arg-NH$_2$,
Ser-Pro-Trp-Ser-Ser-Ala-Ser-Val-Thr-Ala-Gly-Asp-Gly-Val-D-Ile-Thr-Arg-Ile-Arg-NHCH$_2$CH$_3$,
Ac-Ser-Pro-Trp-Ser-Ser-Ala-Ser-Val-Thr-Ala-Gly-Asp-Gly-Val-D-Ile-Thr-Arg-Ile-Arg,
Ac-Ser-Pro-Trp-Ser-Ser-Ala-Ser-Val-Thr-Ala-Gly-Asp-Gly-Val-D-Ile-Thr-Arg-Ile-Arg-NH$_2$,
Ac-Ser-Pro-Trp-Ser-Ser-Ala-Ser-Val-Thr-Ala-Gly-Asp-Gly-Val-D-Ile-Thr-Arg-Ile-Arg-NHCH$_2$CH$_3$,
Gly-D-Val-Ile-D-Thr-D-Arg-D-Ile-D-Arg,
Gly-D-Val-Ile-D-Thr-D-Arg-D-Ile-D-Arg-NH$_2$,
Gly-D-Val-Ile-D-Thr-D-Arg-D-Ile-D-Arg-NHCH$_2$CH$_3$,
Ac-Gly-D-Val-Ile-D-Thr-D-Arg-D-Ile-D-Arg,
Ac-Gly-D-Val-Ile-D-Thr-D-Arg-D-Ile-D-Arg-NH$_2$ and
Ac-Gly-D-Val-Ile-D-Thr-D-Arg-D-Ile-D-Arg-NHCH$_2$CH$_3$,
D-Arg-D-Ile-D-Arg-D-Thr-Ile-D-Val-Gly,
D-Arg-D-Ile-D-Arg-D-Thr-Ile-D-Val-Gly-NH$_2$,
D-Arg-D-Ile-D-Arg-D-Thr-Ile-D-Val-Gly-NHCH$_2$CH$_3$,
Ac-D-Arg-D-Ile-D-Arg-D-Thr-Ile-D-Val-Gly,
Ac-D-Arg-D-Ile-D-Arg-D-Thr-Ile-D-Val-Gly-NH$_2$,
Ac-D-Arg-D-Ile-D-Arg-D-Thr-Ile-D-Val-Gly-NHCH$_2$CH$_3$,
Gly-Val-D-Ile-Lys-Arg-Ile-Arg,
Ac-Gly-Val-D-Ile-Lys-Arg-Ile-Arg,
Gly-Val-D-Ile-Lys-Arg-Ile-Arg-NH$_2$,
Ac-Gly-Val-D-Ile-Lys-Arg-Ile-Arg-NH$_2$,
Gly-Val-D-Ile-Lys-Arg-Ile-Arg-NHCH$_2$CH$_3$,
Ac-Gly-Val-D-Ile-Lys-Arg-Ile-Arg-NHCH$_2$CH$_3$,
Gly-Val-D-Ile-Lys-Arg-Ser-Arg,
Ac-Gly-Val-D-Ile-Lys-Arg-Ser-Arg,
Gly-Val-D-Ile-Lys-Arg-Ser-Arg-NH$_2$,
Ac-Gly-Val-D-Ile-Lys-Arg-Ser-Arg-NH$_2$,
Gly-Val-D-Ile-Lys-Arg-Ser-Arg-NHCH$_2$CH$_3$,
Ac-Gly-Val-D-Ile-Lys-Arg-Ser-Arg-NHCH$_2$CH$_3$,
Gly-Val-D-Ile-Thr-Arg-Ser-Arg,
Ac-Gly-Val-D-Ile-Thr-Arg-Ser-Arg,
Gly-Val-D-Ile-Thr-Arg-Ser-Arg-NH$_2$,
Ac-Gly-Val-D-Ile-Thr-Arg-Ser-Arg-NH$_2$,
Gly-Val-D-Ile-Thr-Arg-Ser-Arg-NHCH$_2$CH$_3$,
Ac-Gly-Val-D-Ile-Thr-Arg-Ser-Arg-NHCH$_2$CH$_3$,
Gly-Val-D-Ile-Tyr-Arg-Ile-Arg,
Ac-Gly-Val-D-Ile-Tyr-Arg-Ile-Arg,
Gly-Val-D-Ile-Tyr-Arg-Ile-Arg-NH$_2$,
Ac-Gly-Val-D-Ile-Tyr-Arg-Ile-Arg-NH$_2$,
Gly-Val-D-Ile-Tyr-Arg-Ile-Arg-NHCH$_2$CH$_3$,
Ac-Gly-Val-D-Ile-Tyr-Arg-Ale-Arg-N, CH$_2$CH$_3$,
Gly-Val-D-Ile-Tyr-Arg-Asn-Arg,
Ac-Gly-Val-D-Ile-Tyr-Arg-Asn-Arg,
Gly-Val-D-Ile-Tyr-Arg-Asn-Arg-NH$_2$,
Ac-Gly-Val-D-Ile-Tyr-Arg-Asn-Arg-NH$_2$,
Gly-Val-D-Ile-Tyr-Arg-Asn-Arg-NHCH$_2$CH$_3$, Ac-Gly-Val-D-Ile-Tyr-Arg-Asn-Arg-NHCH₂CH₃,
Gly-Val-D-Ile-Thr-Arg-Asn-Arg,
Ac-Gly-Val-D-Ile-Thr-Arg-Asn-Arg,
Gly-Val-D-Ile-Thr-Arg-Asn-Arg-NH₂,
Ac-Gly-Val-D-Ile-Thr-Arg-Asn-Arg-NH₂,
Gly-Val-D-Ile-Thr-Arg-Asn-Arg-NHCH₂CH₃,
Ac-Gly-Val-D-Ile-Thr-Arg-Asn-Arg-NHCH₂CH₃,
Ser-Pro-Trp-Ser-D-Ser-Ala-Ser-Val-Thr-Ala-Gly-Asp-Gly-Val-D-Ile-Thr-Arg-Ile-Arg,
Ser-Pro-Trp-Ser-D-Ser-Ala-Ser-Val-Thr-Ala-Gly-Asp-Gly-Val-D-Ile-Thr-Arg-Ile-Arg-NH₂,
Ser-Pro-Trp-Ser-D-Ser-Ala-Ser-Val-Thr-Ala-Gly-Asp-Gly-Val-D-Ile-Thr-Arg-Ile-Arg-NHCH₂CH₃,
Ac-Ser-Pro-Trp-Ser-D-Ser-Ala-Ser-Val-Thr-Ala-Gly-Asp-Gly-Val-D-Ile-Thr-Arg-Ile-Arg,
Ac-Ser-Pro-Trp-Ser-D-Ser-Ala-Ser-Val-Thr-Ala-Gly-Asp-Gly-Val-D-Ile-Thr-Arg-Ile-Arg-NH₂, and
Ac-Ser-Pro-Trp-Ser-D-Ser-Ala-Ser-Val-Thr-Ala-Gly-Asp-Gly-Val-D-Ile-Thr-Arg-Ile-Arg-NHCH₂CH₃,
Ser-Pro-Trp-Ser-D-Ser-Ala-Ser-Val-Thr-Ala-Gly-Asp-Gly-Val-Ile-Thr-Arg-Ile-Arg,
Ser-Pro-Trp-Ser-D-Ser-Ala-Ser-Val-Thr-Ala-Gly-Asp-Gly-Val-Ile-Thr-Arg-Ile-Arg-NH₂,
Ser-Pro-Trp-Ser-D-Ser-Ala-Ser-Val-Thr-Ala-Gly-Asp-Gly-Val-Ile-Thr-Arg-Ile-Arg-NHCH₂CH₃,
Ac-Ser-Pro-Trp-Ser-D-Ser-Ala-Ser-Val-Thr-Ala-Gly-Asp-Gly-Val-Ile-Thr-Arg-Ile-Arg,
Ac-Ser-Pro-Trp-Ser-D-Ser-Ala-Ser-Val-Thr-Ala-Gly-Asp-Gly-Val-Ile-Thr-Arg-Ile-Arg-NH₂,
Ac-Ser-Pro-Trp-Ser-D-Ser-Ala-Ser-Val-Thr-Ala-Gly-Asp-Gly-Val-Ile-Thr-Arg-Ile-Arg-NHCH₂CH₃,
Ser-Pro-Trp-D-Ser-Ser-Ala-Ser-Val-Thr-Ala-Gly-Asp-Gly-Val-Ile-Thr-Arg-Ile-Arg,
Ser-Pro-Trp-D-Ser-Ser-Ala-Ser-Val-Thr-Ala-Gly-Asp-Gly-Val-Ile-Thr-Arg-Ile-Arg-NH₂,
Ser-Pro-Trp-D-Ser-Ser-Ala-Ser-Val-Thr-Ala-Gly-Asp-Gly-Val-Ile-Thr-Arg-Ile-Arg-NHCH₂CH₃,
Ac-Ser-Pro-Trp-D-Ser-Ser-Ala-Ser-Val-Thr-Ala-Gly-Asp-Gly-Val-Ile-Thr-Arg-Ile-Arg,
Ac-Ser-Pro-Trp-D-Ser-Ser-Ala-Ser-Val-Thr-Ala-Gly-Asp-Gly-Val-Ile-Thr-Arg-Ile-Arg-NH₂, and
Ac-Ser-Pro-Trp-D-Ser-Ser-Ala-Ser-Val-Thr-Ala-Gly-Asp-Gly-Val-Ile-Thr-Arg-Ile-Arg-NHCH₂CH₃.

Effect of the Compounds of the Invention on Endothelial Cell Migration

The effect of the peptides of the invention on endothelial cell migration was determined in vitro using the endothelial cell migration assay. This assay was performed essentially as described by Polverini, P. J. et al., *Methods Enzymol*, 198: 440–450 (1991). Briefly, bovine capillary (adrenal) endothelial cells (BCE, supplied by Judah Folkman, Harvard University Medical School) were starved overnight in DMEM containing 0.1% bovine serum albumin (BSA). Cells were then harvested with trypsin and resuspended in DMEM with 0.1% BSA at a concentration of $1.5 \times 10^6$ cells/mL. Cells were added to the bottom of a 48-well modified Boyden chamber (Nucleopore Corporation, Cabin John, Md.). The chamber was assembled and inverted, and cells were allowed to attach for 2 hours at 37° C. to polycarbonate chemotaxis membranes (5 μm pore size) that had been soaked in 0.1 % gelatin overnight and dried. The chamber was then reinverted and test compounds were added to the wells of the upper chamber (to a total volume of 50 μL); the apparatus was then incubated for 4 hours at 37° C. Membranes were recovered, fixed and stained (DiffQuick, Fisher Scientific, Pittsburgh, Pa.) and the number of cells that had migrated to the upper chamber per 10 high power fields were counted. Background migration to DMEM+0.1% BSA was subtracted and the data reported as the number of cells migrated per 10 high power fields (400×) or when results from multiple experiments were combined, as the percent of maximal migration compared to a simultaneous positive control. The compounds of the invention inhibit cell migration as shown in Table 1.

TABLE 1

Effect of the Compounds of the Invention on Endothelial Cell Migration

| Peptide | IC₅₀ (nM) |
| --- | --- |
| Ser-Pro-Trp-Ser-Ser-Ala-Ser-Val-Thr-Ala-Gly-Asp-Gly-Val-D-Ile-Thr-Arg-Ile-Arg | 10 |
| Ac-Gly-Val-D-Ile-Thr-Arg-Ile-Arg-NH₂ | 7 |
| Ac-Gly-Val-D-Ile-Thr-Arg-Ile-Arg-NHEt | 0.67 |
| Ac-Tyr-Gly-Val-D-Ile-Thr-Arg-Ile-Arg-NHEt | 50 |
| Ser-Pro-Trp-Ser-D-Ser-Ala-Ser-Val-Thr-Ala-Gly-Asp-Gly-Val-Ile-Thr-Arg-Ile-Arg | 0.9 |
| Ser-Pro-Trp-Ser-D-Ser-Ala-Ser-Val-Thr-Ala-Gly-Asp-Gly-Val-D-Ile-Thr-Arg-Ile-Arg | 0.9 |

Inhibition of angiogenesis in vivo was measured using a rat corneal neovascularization assay. Accordingly, 6% hydron pellets containing peptide alone or in combination with 0.15 μM bFGF were implanted in rat corneas 1–1.5 mm from the limbus. at 7 days, the rats were sacrificed, perfused with colloidal carbon to visualize vessels and the corneas were extracted. Vigorous vessel ingrowth was scored as a positive angiogenic response. Induction control indicates response to 0.15 μM bFGF alone. Negative controls were done against 0.1% BSA, which does not induce vessel ingrowth. The inhibition of neovasucularization by compounds of the invention is shown in Table 2.

TABLE 2

Inhibition of Rat Corneal Neovascularization by the Compounds of the Invention

| | Positive Corneas/Total Implanted | |
| --- | --- | --- |
| Peptide | Tested Alone | Tested + bFGF |
| Ac-Gly-Val-D-Ile-Thr-Arg-Ile-Arg | 0/3 | 0/3 |
| Ac-Gly-Val-D-Ile-Thr-Arg-Ile-Arg-NH₂ | | |
| 0.1 μM | 0/3 | 1/3 |
| 1 μM | 0/1 | 0/2 |
| 20 μM | 0/4 | 0/2 |
| Ser-Pro-Trp-D-Ser-Ser-Ala-Ser-Val-Thr-Ala-Gly-Asp-Gly-Val-D-Ile-Thr-Arg-Ile-Arg | 0/3 | 0/3 |
| Induction control | not determined | 4/4 |

The compounds of the invention, including but not limited to those specified in the examples, possess anti-angiogenic activity. As angiogenesis inhibitors, such compounds are useful in the treatment of both primary and metastatic solid tumors, including carcinomas of breast, colon, rectum, lung, oropharynx, hypopharynx, esophagus, stomach, pancreas, liver, gallbladder and bile ducts, small intestine, urinary tract (including kidney, bladder and urothelium), female genital tract, (including cervix, uterus, and ovaries as well as choriocarcinoma and gestational trophoblastic disease), male genital tract (including prostate, seminal vesicles, testes and and germ cell tumors), endocrine glands (including the thyroid, adrenal, and pituitary glands), and skin, as well as hemangiomas, melanomas, sarcomas (including those arising from bone and soft tissues as well as Kaposi's sarcoma) and tumors of the brain, nerves, eyes, and meninges (including astrocytomas, gliomas, glioblastomas, retinoblastomas, neuromas, neuroblastomas, Schwannomas, and meningiomas). Such compounds may also be useful in treating solid tumors arising from hematopoietic malignancies such as leukemias (i.e. chloromas, plasmacytomas and the plaques and tumors of mycosis fungoides and cutaneous T-cell lymphoma/leukemia) as well as in the treatment of lymphomas (both Hodgkin's and non-Hodgkin's lymphomas). In addition, these compounds or genes which encode their expression may be useful in the prevention of metastases from the tumors described above either when used alone or in combination with radiotherapy and/or other chemotherapeutic agents.

Further uses include the treatment and prophylaxis of autoimmune diseases such as rheumatoid, immune and degenerative arthritis; various ocular diseases such as diabetic retinopathy, retinopathy of prematurity, corneal graft rejection, retrolental fibroplasia, neovascular glaucoma, rubeosis, retinal neovascularization due to macular degeneration, hypoxia, angiogenesis in the eye associated with infection or surgical intervention, and other abnormal neovascularization conditions of the eye; skin diseases such as psoriasis; blood vessel diseases such as hemagiomas, and capillary proliferation within atherosclerotic plaques; Osler-Webber Syndrome; myocardial angiogenesis; plaque neovascularization; telangiectasia; hemophiliac joints'; angiofibroma; and wound granulation. Other uses include the treatment of diseases characterized by excessive or abnormal stimulation of endothelial cells, including but not limited to intestinal adhesions, Crohn's disease, atherosclerosis, scleroderma, and hypertrophic scars, i.e. keloids. Another use is as a birth control agent, by inhibiting ovulation and establishment of the placenta. The compounds of the invention are also useful in the treatment of diseases that have angiogenesis as a pathologic consequence such as cat scratch disease (*Rochele ninalia quintosa*) and ulcers (*Helicobacter pylori*). The compounds of the invention are also useful to reduce bleeding by administration prior to surgery, especially for the treatment of resectable tumors.

The compounds of the invention may be used in combination with other compositions and procedures for the treatment of diseases. For example, a tumor may be treated conventionally with surgery, radiation or chemotherapy combined with a peptide of the present invention and then a peptide of the present invention may be subsequently administered to the patient to extend the dormancy of micrometastases and to stabilize and inhibit the growth of any residual primary tumor. Additionally, the compounds of the invention may be combined with pharmaceutically acceptable excipients, and optionally sustained-release matrices, such as biodegradable polymers, to form therapeutic compositions.

A sustained-release matrix, as used herein, is a matrix made of materials, usually polymers, which are degradable by enzymatic or acid-base hydrolysis or by dissolution. Once inserted into the body, the matrix is acted upon by enzymes and body fluids. A sustained-release matrix desirably is chosen from biocompatible materials such as liposomes, polylactides (polylactic acid), polyglycolide (polymer of glycolic acid), polylactide co-glycolide (copolymers of lactic acid and glycolic acid) polyanhydrides, poly(ortho)esters, polypeptides, hyaluronic acid, collagen, chondroitin sulfate, carboxcylic acids, fatty acids, phospholipids, polysaccharides, nucleic acids, polyamino acids, amino acids such as phenylalanine, tyrosine, isoleucine, polynucleotides, polyvinyl propylene, polyvinylpyrrolidone and silicone. A preferred biodegradable matrix is a matrix of one of either polylactide, polyglycolide, or polylactide co-glycolide (co-polymers of lactic acid and glycolic acid).

When used in the above or other treatments, a therapeutically effective amount of one of the compounds of the present invention may be employed in pure form or, where such forms exist, in pharmaceutically acceptable salt form. By a "therapeutically effective amount" of the compound of the invention is meant a sufficient amount of the compound to treat an angiogenic disease, (for example, to limit tumor growth or to slow or block tumor metastasis) at a reasonable benefit/risk ratio applicable to any medical treatment. It will be understood, however, that the total daily usage of the compounds and compositions of the present invention will be decided by the attending physician within the scope of sound medical judgment. The specific therapeutically effective dose level for any particular patient will depend upon a variety of factors including the disorder being treated and the severity of the disorder; activity of the specific compound employed; the specific composition employed, the age, body weight, general health, sex and diet of the patient; the time of administration, route of administration, and rate of excretion of the specific compound employed; the duration of the treatment; drugs used in combination or coincidential with the specific compound employed; and like factors well known in the medical arts. For example, it is well within the skill of the art to start doses of the compound at levels lower than those required to achieve the desired therapeutic effect and to gradually increase the dosage until the desired effect is achieved.

The compounds of the present invention can be used in the form of salts derived from inorganic or organic acids. These salts include but are not limited to the following: acetate, adipate, alginate, citrate, aspartate, benzoate, benzenesulfonate, bisulfate, butyrate, camphorate, camphorsufonate, digluconate, glycerophosphate, hemisulfate, heptanoate, hexanoate, fumarate, hydrochloride, hydrobromide, hydroiodide, 2-hydroxyethansulfonate (isethionate), lactate, maleate, methanesulfonate, nicotinate, 2-naphthalenesulfonate, oxalate, pamoate, pectinate, persulfate, 3-phenylpropionate, prcrate, pivalate, propionate, succinate, tartrate, thiocyanate, phosphate, glutamate, bicarbonate, p-toluenesulfonate and undecanoate. Water or oil-soluble or dispersible products are thereby obtained.

Examples of acids which may be employed to form pharmaceutically acceptable acid addition salts include such inorganic acids as hydrochloric acid, sulphuric acid and phosphoric acid and such organic acids as maleic acid, succinic acid and citric acid. Other salts include salts with alkali metals or alkaline earth metals, such as sodium, potassium, calcium or magnesium or with organic basis. Preferred salts of the compounds of the invention include phosphate, tris and acetate.

The total daily dose of the compounds of this invention administered to a human or lower animal may range from about 0.001 to about 1 mg/kg of patients body mass/day. If desired, the effective daily dose may be divided into multiple doses for purposes of administration; consequently, single dose compositions may contain such amounts or submultiples thereof to make up the daily dose.

Alternatively, a compound of the present invention may be administered as pharmaceutical compositions containing the compound of interest in combination with one or more pharmaceutically acceptable excipients. A pharmaceutically acceptable carrier or excipient refers to a non-toxic solid, semi-solid or liquid filler, diluent, encapsulating material or formulation auxiliary of any type. The compositions may be administered parenterally, intracisternally, intravaginally, intraperitoneally, topically (as by powders, ointments, drops or transdermal patch), rectally, or bucally. The term "parenteral" as used herein refers to modes of administration which include intravenous, intramuscular, intraperitoneal, intrasternal, subcutaneous and intraarticular injection and infusion.

Pharmaceutical compositions for parenteral injection comprise pharmaceutically-acceptable sterile aqueous or nonaqueous solutions, dispersions, suspensions or emulsions, as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol, and the like), carboxymethylcellulose and suitable mixtures thereof, vegetable oils (such as olive oil), and injectable organic esters such as ethyl oleate. Proper fluidity may be maintained, for example, by the use of coating materials such as lecithin, by the maintenance of the required particle size in the case of dispersions, and by the use of surfactants.

These compositions may also contain adjuvants such as preservative, wetting agents, emulsifying agents, and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents such as sugars, sodium chloride, and the like. Prolonged absorption of the injectable pharmaceutical form may be brought about by the inclusion of agents which delay absorption, such as aluminum monostearate and gelatin.

Injectable depot forms are made by forming microencapsule matrices of the drug in biodegradable polymers such as polylactide-polyglycolide, poly(orthoesters) and poly(anhydrides). Depending upon the ratio of drug to polymer and the nature of the particular polymer employed, the rate of drug release can be controlled. Depot injectable formulations are also prepared by entrapping the drug in liposomes or microemulsions which are compatible with body tissues.

The injectable formulations may be sterilized, for example, by filtration through a bacterial-retaining filter, or by incorporating sterilizing agents in the form of sterile solid compositions which can be dissolved or dispersed in sterile water or other sterile injectable medium just prior to use.

Topical administration includes administration to the skin or mucosa, including surfaces of the lung and eye. Compositions for topical administration, including those for inhalation, may be prepared as a dry powder which may be pressurized or non-pressurized. In non-pressurized powder compositions, the active ingredient in finely divided form may be used in admixture with a larger-sized pharmaceutically-acceptable inert carrier comprising particles having a size, for example, of up to 100 micrometers in diameter. Suitable inert carriers include sugars such as lactose. Desirably, at least 95% by weight of the particles of the active ingredient have an effective particle size in the range of 0.01 to 10 micrometers.

Alternatively, the composition may be pressurized and contain a compressed gas, such as nitrogen or a liquified gas propellant. The liquified propellant medium and indeed the total composition is preferably such that the active ingredient does not dissolve therein to any substantial extent. The pressurized composition may also contain a surface active agent, such as a liquid or solid non-ionic surface active agent or may be a solid anionic surface active agent It is preferred to use the solid anionic surface active agent in the form of a sodium salt.

A further form of topical administration is to the eye. A compound of the invention is delivered in a pharmaceutically acceptable ophthalmic vehicle, such that the compound is maintained in contact with the ocular surface for a sufficient time period to allow the compound to penetrate the corneal and internal regions of the eye, as for example the anterior chamber, posterior chamber, vitreous body, aqueous humor, vitreous humor, cornea, iris/ciliary, lens, choroid/retina and sclera. The pharmaceutically-acceptable ophthalmic vehicle may, for example, be an ointment, vegetable oil or an encapsulating material. Alternatively, the compounds of the invention may be injected directly into the vitreous and aqueous humour.

Compositions for rectal or vaginal administration are preferably suppositories which may be prepared by mixing the compounds of this invention with suitable non-irritating excipients or carriers such as cocoa butter, polyethylene glycol or a suppository wax which are solid at room temperature but liquid at body temperature and therefore melt in the rectum or vaginal cavity and release the active compound.

Compounds of the present invention may also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically-acceptable and metabolizable lipid capable of forming liposomes can be used. The present compositions in liposome form can contain, in addition to a compound of the present invention, stabilizers, preservatives, excipients, and the like. The preferred lipids are the phospholipids and the phosphatidyl cholines (lecithins), both natural and synthetic. Methods to form liposomes are known in the art. See, for example, Prescott, Ed., *Methods in Cell Biology*, Volume XIV, Academic Press, New York, N.Y. (1976), p. 33 et seq.

While the compounds of the invention can be administered as the sole active pharmaceutical agent, they may also be used in combination with one or more agents which are conventionally administered to patients for treating angiogenic diseases. For example, the compounds of the invention are effective over the short term to make tumors more sensitive to traditional cytotoxic therapies such as chemicals and radiation. The compounds of the invention also enhance the effectiveness of existing cytotoxic adjuvant anti-cancer therapies. The compounds of the invention may also be combined with other antiangiogenic agents to enhance their effectiveness, or combined with other antiangiogenic agents and administered together with other cytotoxic agents. In particular, when used in the treatment of solid tumors, compounds of the invention may be administered with IL-12, retinoids, interferons, angiostatin, endostatin, thalidomide, thrombospondin-1, thrombospondin-2, captopryl, anti-neoplastic agents such as alpha inteferon, COMP (cyclophosphamide, vincristine, methotrexate and prednisone), etoposide, mBACOD (methortrexate, bleomycin, doxorubicin, cyclophosphamide, vincristine and dexamethasone), PRO-MACE/MOPP (prednisone, methotrexate (w/leucovin rescue), doxorubicin, cyclophosphamide, taxol, etoposide/mechlorethamine, vincristine, prednisone and procarbazine), vincristine, vinblastine, angioinhibins, TNP-470, pentosan polysulfate, platelet factor 4, angiostatin, LM-609, SU-101, CM-101, Techgalan, thalidomide, SP-PG and the like as well as with rediation.

Total daily dose of the compositions of the invention to be administered to a human or other mammal host in single or divided doses may be in amounts, for example, from 0.0001 to 300 mg/kg body weight daily and more usually 1 to 300 mg/kg body weight.

It will be understood that agents which can be combined with the compound of the present invention for the inhibition, treatment or prophylaxis of angiogenic diseases are not limited to those listed above, but include in principle any agents useful for the treatment or prophylaxis of angiogenic diseases.

The peptides of the invention may be used for the development of affinity columns for isolation of receptors relevant to the antiangiogenic activity of the peptide of the invention, e.g. TSP-1 receptor, in, for example, cultured endothelial cells. As is known in the art, isolation and purification of the receptor may be followed by amino acid sequencing to identify and isolate polynucleotides which encode the receptor. Recombinant expression of this receptor would allow greater amounts of receptor to be produced, e.g. to produce a sufficient quantity for use in high throughput screening assays to identify other angiogenesis inhibitors.

The peptides of the present invention may be chemically coupled to isotopes, enzymes, carrier proteins, cytotoxic agents, fluorescent molecules, chemiluminescent, bioluminescent and other compounds for a variety of applications. For example, a peptide may be labeled to facilitate testing of its ability to bind antisera or to detect cell types which possess a relevant receptor. The coupling technique is generally chosen on the basis of the functional groups available on the amino acids of the peptide including, but not limited to amino, sulfhydral, carboxyl, amide, phenol, and imidazole. Various reagents used to effect such couplings include among others, glutaraldehyde, dizodized benzidine, carbodiimide, and p-benzoquinone.

The efficiency of the coupling reaction is determined using different techniques appropriate for the specific reaction. For example, radiolabeling of the peptide with $I^{125}$ may be accomplished using chloramine T and $NaI^{125}$ of high specific activity. The reaction is terminated with sodium metabisulfite and the mixture is desalted on disposable columns. The labeled peptide is eluted from the column and fractions are collected. Aliquots are removed from each fraction and radioactivity measured in a gamma counter. In this manner, a labeled peptide may be obtained which is free from unreacted $NaI^{125}$.

The peptides of the present invention can also be used as antigens to generate polyclonal or monoclonal antibodies. Such antibodies can be used in diagnostic methods and kits to detect or quantify the peptide of the invention, or peptides related thereto, in a body fluid or tissue. Results from these tests could be used to diagnose or determine the prognostic relevance of such peptides.

The use of the peptides of the present invention to generate monoclonal antibodies in animals such as the mouse, rabbit or sheep, follows techniques well known in the art. If desired, the antibodies can then be used to make anti-idiotype atibodies which in turn can be humanized as is known in the art to prevent immunological responses. The humanized antibodies can be used to inhibit angiogenesis or to make kits to detect the receptor as described herein.

For the production of polyclonal antisera in rabbits, sheep, goats or other animals the peptides of the invention are coupled, for example through lysine residues, to purified bovine serum albumin using glutaraldehyde. The efficiency of this reaction may be determined by measuring the incorporation of radiolabeled peptide. Unreacted glutaraldehyde and peptide may be separated by dialysis and the conjugate stored for subsequent use.

Serum samples from generation of polyclonal antisera or media samples from production of monoclonal antisera may be analyzed for determination of antibody titer and in particular, for the determination of high titer antisera Subsequently, the highest titer antisera may be tested to establish the following; a) optimal antiserum dilution for highest specific binding of the antigen and lowest non-specific binding, b) ability to bind increasing amounts of peptide in a standard displacement curve, c) potential cross-reactivity with immunologically-related peptides and proteins (including plasminogen, TSP-1, and TSP-1 of related species), and d) ability to detect the peptide of the invention in extracts of plasma, urine, tissues, and in cell culture media.

Titer may be established through several means known in the art, such as by dot blot and density analysis, and also by precipitation of radiolabeled peptide-antibody complexes using protein A, secondary antisera, cold ethanol or charcoal-dextran followed by activity measurement with a gamma counter. If desired, the highest titer antisera may be purified on affinity columns. For example, the peptides of the invention may be coupled to a commercially available resin and used to form an affinity column. Antiserum samples may then be passed through the column so that antibodies to the peptides of the invention bind (via the peptide) to the column. These bound antibodies are subsequently eluted, collected and evaluated for determination of titer and specificity.

Kits for measurement of the compounds of the invention are also contemplated as part of the present invention. Antisera that possess the highest titer and specificity and can detect the peptides of the invention in extracts of plasma, urine, tissues, and in cell culture media may be used to establish assay kits for rapid, reliable, sensitive, and specific measurement and localization of peptides of the invention. These assay kits may employ (but are not limited to) the following techniques: competitive and non-competitive assays, radioimmunoassay (RIA), bioluminescence and chemilurninescence assays, fluorometric assays, sandwich assays, immunoradiometric assays, dot blots, enzyme linked assays including ELISA, microtiter plates, antibody coated strips or dipsticks for rapid monitoring of urine or blood, and immunocytochemistry. For each kit the range, sensitivity, precision, reliability, specificity and reproducibility of the assay are established by means well known to those skilled in the art.

The above described assay kit would provide instructions, antiserum, one or more peptides of the invention, and possibly radiolabeled peptides of the invention and/or reagents for precipitation of bound peptide/antibody complexes. Such a kit would be useful for the measurement of the peptide of the invention in biological fluids and tissue extracts of animals and humans with and without tumors, as is well known in the art.

Another kit may be used to visualize or localize the peptide of the invention in tissues and cells. Immunohistochemistry techniques and kits, for example, which employ such techniques are well known to those of ordinary skill in the art. Such a kit provide antisera to the peptide of the invention, and possibly blocking serum and secondary antiserum linked to a fluorescent molecule such as fluorescein isothiocyanate, or to some other reagent used to visualize the primary antiserum. Using this methodology, biopsied tumors may be examined for sites of peptide production or for sites of the peptide receptor. Alternatively, a kit may supply radiolabeled nucleic acids for use in in situ hybridization to probe for messenger RNA which encodes the compound of the invention.

Synthesis of the Peptides

The polypeptides of the present invention may be synthesized by any techniques that are known to those skilled in the art. For solid phase peptide synthesis, a summary of the many techniques may be found in J. M. Stewart and J. D. Young, *Solid Phase Peptide Synthesis*, W. H. Freeman Co. (San Francisco), 1963 and J. Meienhofer, *Hormonal Proteins and Peptides*, vol. 2, p. 46, Academic Press (New York), 1973. For classical solution synthesis see G. Schroder and K. Lupke, *The Peptides*, vol. 1, Acacemic Press (New York), 1965.

In general, these methods comprise the sequential addition of one or more amino acids or suitably protected amino acids to a growing peptide chain. Normally, either the amino or carboxyl group of the first amino acid is protected by a suitable protecting group. The protected or derivatized amino acid can then either attached to an inert solid support or utilized in solution by adding the next amino acid in the sequence having the complimentary (amino or carboxyl) group suitably protected, under conditions suitable for forming the amide linkage. The protecting group is then removed from this newly added amino acid residue and the next amino acid (suitably protected) is then added, and so forth. After all the desired amino acids have been linked in the proper sequence, any remaining protecting groups (and any solid support) are removed sequentially or concurrently, to afford the final polypeptide. By simple modification of this general procedure, it is possible to add more than one amino acid at a time to a growing chain, for example, by coupling (under conditions which do not racemize chiral centers) a protected tripeptide with a properly protected dipeptide to form, after deprotection, a pentapeptide.

A particularly preferred method of preparing compounds of the present invention involves solid phase peptide synthesis.

In this particularly preferred method the alpha-amino function is protected by an acid or base sensitive group. Such protecting groups should have the properties of being stable to the conditions of peptide linkage formation, while being readily removable without destruction of the growing peptide chain or racemization of any of the chiral centers contained therein. Suitable protecting groups are 9-fluorenylmethyloxycarbonyl (Fmoc), t-butyloxycarbonyl (Boc), benzyloxycarbonyl (Cbz), biphenylisopropyloxycarbonyl, t-amyloxycarbonyl, isobornyloxycarbonyl, (α,α)dimethyl-3,5-dimethoxybenzyloxycarbonyl, o-nitrophenylsulfenyl, 2-cyano-t-butyloxycarbonyl, and the like. The 9-fluorenylmethyloxycarbonyl (Fmoc) protecting group is preferred.

Particularly preferred side chain protecting groups are, for side chain amino groups as in lysine and arginine: 2,2,5,7,8-pentamethylchroman-6-sulfonyl (pmc), nitro, p-toluenesulfonyl, 4-methoxybenzenesulfonyl, Cbz, Boc, and adamantyloxycarbonyl; for tyrosine: benzyl, o-bromobenzyloxycarbonyl, 2,6-dichlorobenzyl, isopropyl, t-butyl (t-Bu), cyclohexyl, cyclopenyl and acetyl (Ac); for serine: t-butyl, benzyl and tetrahydropyranyl; for histidine: trityl, benzyl, Cbz, p-toluenesulfonyl and 2,4-dinitrophenyl; for tryptophan: formyl.

In the solid phase peptide synthesis method, the C-terminal amino acid is attached to a suitable solid support or resin. Suitable solid supports useful for the above synthesis are those materials which are inert to the reagents and reaction conditions of the stepwise condensation-deprotection reactions, as well as being insoluble in the media used. The preferred solid support for synthesis of C-terminal carboxy peptides is 4-hydroxymethylphenoxymethyl-copoly(styrene-1% divinylbenzene). The preferred solid support for C-terminal amide peptides is 4-(2',4'-dimethoxyphenyl-Fmoc-aminomethyl)phenoxyacetamidoethyl resin available from Applied Biosystems [city, state].

The C-terminal amino acid is coupled to the resin by means of N,N'-dicyclohexylcarbodiimide (DCC), N,N'-diisopropylcarbodiimide (DIC) or O-benzotriazol-1-yl-N,N,N',N'-tetramethyluroniumhexafluorophosphate (HBTU), with or without 4-dimethylaminopyridine (DMAP), 1-hydroxybenzotriazole (HOBT), benzotriazol-1-yloxy-tris (dimethylamino)phosphoniumhexafluorophosphate (BOP) or bis(2-oxo-3-oxazolidinyl)phosphine chloride (BOPCl), mediated coupling for from about 1 to about 24 hours at a temperature of between 100 and 50° C. in a solvent such as dichloromethane or DMF. When the solid support is 4-(2',4'-dimethoxyphenyl-Fmoc-aminomethyl) phenoxyacetamidoethyl resin, the Fmoc group is cleaved with a secondary amine, preferably piperidine, prior to coupling with the C-terminal amino acid as described above. The preferred method for coupling to the deprotected 4-(2',4'-dimethoxyphenyl-Fmoc-aminomethyl) phenoxyacetamidoethyl resin is is O-benzotriazol-1-yl-N,N,N',N'-tetramethyluroniumhexafluorophosphate (HBTU, 1 equiv.) and 1-hydroxybenzotriazole (HOBT, 1 equiv.) in DMF.

The coupling of successive protected amino acids can be carried out in an automatic polypeptide synthesizer as is well known in the art. In a preferred embodiment, the α-amino function in the amino acids of the growing peptide chain are protected with Fmoc. The removal of the Fmoc protecting group from the N-terminal side of the growing peptide is accomplished by treatment with a secondary amine, preferably piperidine. Each protected amino acid is then introduced in about 3-fold molar excess and the coupling is preferably carried out in DMF. The coupling agent is normally O-benzotriazol-1-yl-N,N,N',N'-tetramethyluroniumhexafluorophosphate (HBTU, 1 equiv.) and 1-hydroxybenzotriazole (HOBT, 1 equiv.).

At the end of the solid phase synthesis, the polypeptide is removed from the resin and deprotected, either in successively or in a single operation. Removal of the polypeptide and deprotection can be accomplished in a single operation by treating the resin-bound polypeptide with a cleavage reagent, for example thianisole, water, ethanedithiol and trifluoroacetic acid.

In cases wherein the C-terminus of the polypeptide is an alkylamide, the resin is cleaved by aminolysis with an alkylamine. Alternatively, the peptide may be removed by transesterification, e.g. with methanol, followed by aminolysis or by direct transamidation. The protected peptide may be purified at this point or taken to the next step directly. The removal of the side chain protecting groups is accomplished using the cleavage cocktail described above.

The fully deprotected peptide is purified by a sequence of chromatographic steps employing any or all of the following types: ion exchange on a weakly basic resin in the acetate form; hydrophobic adsorption chromatography on underivitized polystyrene-divinylbenzene (for example, AMBERLITE® XAD); silica gel adsorption chromatography; ion exchange chromatography on carboxymethylcellulose; partition chromatography, e.g. on SEPHADEX® G-25, LH-20 or countercurrent distribution; high performance liquid chromatography (HPLC), especially reverse-phase HPLC on octyl- or octadecylsilyl-silica bonded phase column packing.

The following examples will serve to further illustrate the preparation of the novel compounds of the invention.

Preparation of the Cleavage Reagent

The cleavage reagent (2 mL) is prepared by mixing, in the following order, thioanisole g(100 µL), water (50 µL), ethanedithiol (50 µL) and trifluoroacetic acid (1.8 mL). The freshly-prepared mixture is cooled to −5° C. to −10° C. and used as described below.

Cleavage Procedure

A mixture of resin-bound polypeptide and cleavage reagent is stirred at 0° C. for 10–15 minutes and then at ambient temperature for a further 1.75 hours. The amount of time is increased by 0.5 hours for each additional arginine up to a total of three hours. The amount of cleavage reagent used is determined using the following formula:

| weight of resin (mg) | amount of cleavage reagent (µL) |
|---|---|
| 0–10 | 100 |
| 10–25 | 200 |
| 25–50 | 400 |
| 50–100 | 700 |
| 100–200 | 1200 |

The resin is then filtered off and rinsed with neat trifluoroacetic acid. The filtrate is then added in 0.5 mL portions to a centrifuge tube containing about 8 mL of cold diethyl ether. The suspension is then centrifuged and the supernatant is decanted off. The pellet is re-suspended in about 8 mL of ether, another 0.5 mL of the filtrate is added, and the process is repeated until all of the peptide is precipitated. The precipitated filtrate is then washed with ether, dried and lyophilized.

If the peptide does not precipitate upon addition to ether, the mixture is shaken with aqueous 30% acetic acid. The organic phase is then extracted twice with aqueous 30% acetic acid and the combined aqueous extracts are lyophilized.

EXAMPLE 1

Gly-Asp-Gly-Val-D-Ile-Thr-Arg-Ile-Arg

In the peptide synthesis column position of a Perkin Elmer/Applied Biosynthesis SYNERGY® peptide synthesizer is placed an Arg(Pmc) peptide synthesis column (25 µM amino acid; Applied Biosystems). Amino acids are added sequentially according to the following synthetic cycle:
0. Solvating the resin using DMF for about 5 minutes;
1. Deblocking to remove the Fmoc group from the α-amino acid function using piperidine in DMF for about 15 minutes;
2. Washing with DMF for about 5 minutes;
3. Activating the incoming Fmoc protected amino acid (75 µM) using a 0.2M solution of HBTU (75 µM) and HOBT (75 µM) in DMSO-NMP (N-methylpyrrolidone) and a 0.4M solution of diisopropylethylamine (150 µM) in DMSO-NMP;
4. Coupling using a solution in DMF of the activated Fmoc protected amino acid prepared in step 3 above for about 30 minutes; and
5. Washing with DMF for 5 minutes.

The amino acids are coupled to the resin in the following order using the conditions indicated.

| # Amino Acid | Coupling |
|---|---|
| 1. Fmoc-Ile | 30 minutes |
| 2. Fmoc-Arg(Pmc) | 30 minutes |
| 3. Fmoc-Thr(t-Bu) | 30 minutes |
| 4. Fmoc-D-Ile | 30 minutes |
| 5. Fmoc-Val | 30 minutes |
| 6. Fmoc-Gly | 30 minutes |
| 7. Fmoc-Asp(O-tBu) | 30 minutes |
| 8. Fmoc-Gly | 30 minutes |

Upon completion of the synthesis, the resin is washed with THF for about 5 minutes to remove DMF and shrink the resin. The resin is then gas dried with argon for about 10 minutes and nitrogen for a further 10 minutes to give the resin-bound peptide (80 mg).

Cleavage is accomplished using the procedure described above (40 mg of dry resin-bound peptide, 700 µL of cleavage reagent, cleavage time 2.5 hours) to give the crude peptide (14 mg). Purification by HPLC using a 7 µm Symmetry Prep C18 column (7.8×300 mm) with solvent mixtures varying in a gradient from 5% to 100% acetonitrile-water with 0.1% by volume trifluoroacetic acid over a period of 50 minutes followed by lyophilization gives Gly-Asp-Gly-Val-D-Ile-Thr-Arg-Ile-Arg (5 mg). MS (FAB) m/z 986 (M+H)$^+$.

EXAMPLE 2

Ac-Gly-Asp-Gly-Val-D-Ile-Thr-Arg-Ile-Arg

The desired peptide is prepared by placing 40 mg of the resin bound peptide prepared in Example 1 in the peptide synthesizer and repeating steps 3–5 above except substituting acetic acid (87 µM) for the Fmoc protected amino acid and using 87 µM each of HBTU and HOBT. Cleavage and HPLC purification (gradient from 15% to 100% acetonitrile-water) as described in Example 1 gave Ac-Gly-Asp-Gly-Val-D-Ile-Thr-Arg-Ile-Arg (4 mg).

EXAMPLE 3

Gly-Asp-Gly-Val-D-Ile-Thr-Arg-Ile-Arg-NH$_2$

The desired compound is prepared according to the method of Example 1, except using amide synthesis resin in the synthesis column of the peptide synthesizer. The amino acids are coupled to the resin using the conditions indicated.

| # Amino Acid | Coupling |
|---|---|
| 1. Fmoc-Arg(Pmc) | 30 minutes |
| 2. Fmoc-Ile | 30 minutes |
| 3. Fmoc-Arg(Pmc) | 30 minutes |
| 4. Fmoc-Thr(t-Bu) | 30 minutes |
| 5. Fmoc-D-Ile | 30 minutes |
| 6. Fmoc-Val | 30 minutes |
| 7. Fmoc-Gly | 30 minutes |
| 8. Fmoc-Asp(O-tBu) | 30 minutes |
| 9. Fmoc-Gly | 30 minutes |

EXAMPLE 4

Ac-Gly-Asp-Gly-Val-D-Ile-Thr-Arg-Ile-Arg-NH$_2$

The desired compound is prepared according to the method of Example 2 using the resin-bound peptide prepared in Example 3.

EXAMPLE 5

Gly-Asp-Gly-Val-D-Ile-Thr-Arg-Ile-Arg-NHCH$_2$CH$_3$

Step 1

Gly-Asp(Pmc)-Gly-Val-D-Ile-Thr(t-Bu)-Arg(Pmc)-Ile-Arg(Pmc)-NHCH$_2$CH$_3$

A mixture of peptide-bound resin prepared as in Example 1 and ethylamine is sealed in a vial and stirred for 4 hours. The ethylamine is then evaporated and the methanol is added to the residue. The mixture is filtered and the filtrated concentrated in vacuo. The residue is taken up in methanol-water (3:7) and lyophilized to give the protected peptide.

Step 2

Gly-Asp-Gly-Val-D-Ile-Thr-Arg-Ile-Arg-NHCH$_2$CH$_3$

The desired compound is prepared by deprotection of the peptide prepared in step 1 using the cleavage reagent and procedure described above.

EXAMPLE 6

Gly-Val-D-Ile-Thr-Arg-Ile-Arg

The desired compound is prepared according to the method of Example 1 by coupling the amino acids to the resin in the following order using the conditions indicated.

| # Amino Acid | Coupling |
|---|---|
| 1. Fmoc-Ile | 30 minutes |
| 2. Fmoc-Arg(Pmc) | 30 minutes |
| 3. Fmoc-Thr(t-Bu) | 30 minutes |
| 4. Fmoc-D-Ile | 30 minutes |
| 5. Fmoc-Val | 30 minutes |
| 6. Fmoc-Gly | 30 minutes |

EXAMPLE 7

Ac-Gly-Val-D-Ile-Thr-Arg-Ile-Arg

The desired compound is prepared according to the method of Example 2, except using the resin-bound peptide prepared as in Example 6. MS (FAB) m/z 856 (M+H)$^+$.

EXAMPLE 8

Gly-Val-D-Ile-Thr-Arg-Ile-Arg-NH$_2$

The desired compound is prepared according to the method of Example 3, by coupling the amino acids to the resin in the following order using the conditions indicated.

| # Amino Acid | Coupling |
|---|---|
| 1. Fmoc-Arg(Pmc) | 30 minutes |
| 2. Fmoc-Ile | 30 minutes |
| 3. Fmoc-Arg(Pmc) | 30 minutes |
| 4. Fmoc-Thr(t-Bu) | 30 minutes |
| 5. Fmoc-D-Ile | 30 minutes |
| 6. Fmoc-Val | 30 minutes |
| 7. Fmoc-Gly | 30 minutes |

EXAMPLE 9

Ac-Gly-Val-D-Ile-Thr-Arg-Ile-Arg-NH$_2$

The desired compound is prepared according to the method of Example 2, except using the resin-bound peptide prepared as in Example 8. MS (FAB) m/z 855 (M+H)$^+$, 877 (M+Na)$^+$.

EXAMPLE 10

Gly-Val-D-Ile-Thr-Arg-Ile-Arg-NHCH$_2$CH$_3$

The desired peptide is prepared according to the method of Example 5, except substituting the resin-bound peptide of Example 6 for the resin-bound peptide of Example 1.

EXAMPLE 11

Ac-Gly-Val-D-Ile-Thr-Arg-Ile-Arg-NHCH$_2$CH$_3$

The desired compound is prepared from the resin-bound Ac-Gly-Val-D-Ile-Thr-Arg-Ile-Arg of Example 7 using the method of Example 5. MS (FAB) m/z 883 (M+H)$^+$.

EXAMPLE 12

Tyr-Gly-Val-D-Ile-Thr-Arg-Ile-Arg

The desired compound is prepared according to the method of Example 1 by coupling the amino acids to the resin in the following order using the conditions indicated.

| # Amino Acid | Coupling |
|---|---|
| 1. Fmoc-Ile | 30 minutes |
| 2. Fmoc-Arg(Pmc) | 30 minutes |
| 3. Fmoc-Thr(t-Bu) | 30 minutes |
| 4. Fmoc-D-Ile | 30 minutes |
| 5. Fmoc-Val | 30 minutes |
| 6. Fmoc-Gly | 30 minutes |
| 7. Fmoc-Tyr(tBu) | 30 minutes |

EXAMPLE 13

Tyr-Gly-Val-D-Ile-Thr-Arg-Ile-Arg-NH$_2$

The desired compound is prepared according to the method of Example 3, by coupling the amino acids to the resin in the following order using the conditions indicated.

| # Amino Acid | Coupling |
|---|---|
| 1. Fmoc-Arg(Pmc) | 30 minutes |
| 2. Fmoc-Ile | 30 minutes |
| 3. Fmoc-Arg(Pmc) | 30 minutes |
| 4. Fmoc-Thr(t-Bu) | 30 minutes |
| 5. Fmoc-D-Ile | 30 minutes |
| 6. Fmoc-Val | 30 minutes |
| 7. Fmoc-Gly | 30 minutes |
| 8. Fmoc-Tyr(tBu) | 30 minutes |

EXAMPLE 14

Tyr-Gly-Val-D-Ile-Thr-Arg-Ile-Arg-NHCH$_2$CH$_3$

The desired compound is prepared from the resin-bound peptide of Example 12 using the method of Example 5.

EXAMPLE 15

Ac-Tyr-Gly-Val-D-Ile-Thr-Arg-Ile-Arg

The desired compound is prepared from the resin-bound peptide of Example 12 according to the method of Example 2.

EXAMPLE 16

Ac-Tyr-Gly-Val-D-Ile-Thr-Arg-Ile-Arg-NH$_2$

The desired compound is prepared from the resin-bound peptide of Example 13 according to the method of Example 2. MS (FAB) m/z 1018 (M+H)$^+$.

EXAMPLE 17

Ac-Tyr-Gly-Val-D-Ile-Thr-Arg-Ile-Arg-NHCH$_2$CH$_3$

The desired compound is prepared from the resin-bound Ac-Tyr-Gly-Val-D-Ile-Thr-Arg-Ile-Arg using the method of Example 5.

EXAMPLE 18

Ser-Pro-Trp-Ser-Ser-Ala-Ser-Val-Thr-Ala-Gly-Asp-Gly-Val-D-Ile-Thr-Arg-Ile-Arg

The desired compound is prepared according to the method of Example 1 by coupling the amino acids to the resin in the following order using the conditions indicated.

| # Amino Acid | Coupling |
|---|---|
| 1. Fmoc-Ile | 30 minutes |
| 2. Fmoc-Arg(Pmc) | 30 minutes |
| 3. Fmoc-Thr(t-Bu) | 30 minutes |
| 4. Fmoc-D-Ile | 30 minutes |
| 5. Fmoc-Val | 30 minutes |
| 6. Fmoc-Gly | 30 minutes |
| 7. Fmoc-Asp(O-tBu) | 30 minutes |
| 8. Fmoc-Gly | 30 minutes |
| 9. Fmoc-Ala | 30 minutes |
| 10. Fmoc-Thr(t-Bu) | 30 minutes |
| 11. Fmoc-Val | 30 minutes |
| 12. Fmoc-Ser(tBu) | 30 minutes |
| 13. Fmoc-Ala | 30 minutes |
| 14. Fmoc-Ser(tBu) | 30 minutes |
| 15. Fmoc-Ser(tBu) | 30 minutes |
| 16. Fmoc-Trp | 30 minutes |
| 17. Fmoc-Pro | 30 minutes |
| 18. Fmoc-Ser(tBu) | 30 minutes |

EXAMPLE 19

Ser-Pro-Trp-Ser-Ser-Ala-Ser-Val-Thr-Ala-Gly-Asp-Gly-Val-D-Ile-Thr-Arg-Ile-Arg-NH$_2$

The desired compound is prepared according to the method of Example 3, by coupling the amino acids to the resin in the following order using the conditions indicated.

| # Amino Acid | Coupling |
|---|---|
| 1. Fmoc-Arg(Pmc) | 30 minutes |
| 2. Fmoc-Ile | 30 minutes |
| 3. Fmoc-Arg(Pmc) | 30 minutes |
| 4. Fmoc-Thr(t-Bu) | 30 minutes |
| 5. Fmoc-D-lle | 30 minutes |
| 6. Fmoc-Val | 30 minutes |
| 7. Fmoc-Gly | 30 minutes |
| 8. Fmoc-Asp(O-tBu) | 30 minutes |
| 9. Fmoc-Gly | 30 minutes |
| 10. Fmoc-Ala | 30 minutes |
| 11. Fmoc-Thr(t-Bu) | 30 minutes |
| 12. Fmoc-Val | 30 minutes |
| 13. Fmoc-Ser(tBu) | 30 minutes |
| 14. Fmoc-Ala | 30 minutes |
| 15. Fmoc-Ser(tBu) | 30 minutes |
| 16. Fmoc-Ser(tBu) | 30 minutes |
| 17. Fmoc-Trp | 30 minutes |
| 18. Fmoc-Pro | 30 minutes |
| 19. Fmoc-Ser(tBu) | 30 minutes |

EXAMPLE 20

Ser-Pro-Trp-Ser-Ser-Ala-Ser-Val-Thr-Ala-Gly-Asp-Gly-Val-D-Ile-Thr-Arg-Ile-Arg-NHCH$_2$CH$_3$

The desired peptide is prepared from the resin-bound peptide of Example 19 using the procedure of Example 5.

EXAMPLE 21

Ac-Ser-Pro-Trp-Ser-Ser-Ala-Ser-Val-Thr-Ala-Gly-Asp-Gly-Val-D-Ile-Thr-Arg-Ile-Arg

The desired compound is prepared from the resin bound peptide of Example 18 using the method of Example 2.

EXAMPLE 22

Ac-Ser-Pro-Trp-Ser-Ser-Ala-Ser-Val-Thr-Ala-Gly-Asp-Gly-Val-D-Ile-Thr-Arg-Ile-Arg-NH$_2$

The desired compound is prepared from the resin-bound peptide of Example 19 using the procedure of Example 2.

EXAMPLE 23

Ac-Ser-Pro-Trp-Ser-Ser-Ala-Ser-Val-Thr-Ala-Gly-Asp-Gly-Val-D-Ile-Thr-Arg-Ile-Arg-NHCH$_2$CH$_3$

The desired compound is prepared from the resin-bound peptide of Example 21 using the procedure of Example 5.

EXAMPLE 24

D-Tyr-Gly-Val-D-Ile-Thr-Arg-Ile-Arg

The desired compound is prepared according to the method of Example 1 by coupling the amino acids to the resin in the following order using the conditions indicated.

| # Amino Acid | Coupling |
|---|---|
| 1. Fmoc-Ile | 30 minutes |
| 2. Fmoc-Arg(Pmc) | 30 minutes |
| 3. Fmoc-Thr(t-Bu) | 30 minutes |
| 4. Fmoc-D-Ile | 30 minutes |
| 5. Fmoc-Val | 30 minutes |
| 6. Fmoc-Gly | 30 minutes |
| 7. Fmoc-D-Tyr(tBu) | 30 minutes |

EXAMPLE 25

D-Tyr-Gly-Val-D-Ile-Thr-Arg-Ile-Arg-NH$_2$

The desired compound is prepared according to the method of Example 3, by coupling the amino acids to the resin in the following order using the conditions indicated.

| # Amino Acid | Coupling |
|---|---|
| 1. Fmoc-Arg(Pmc) | 30 minutes |
| 2. Fmoc-Ile | 30 minutes |
| 3. Fmoc-Arg(Pmc) | 30 minutes |
| 4. Fmoc-Thr(t-Bu) | 30 minutes |
| 5. Fmoc-D-Ile | 30 minutes |
| 6. Fmoc-Val | 30 minutes |
| 7. Fmoc-Gly | 30 minutes |
| 8. Fmoc-D-Tyr(tBu) | 30 minutes |

EXAMPLE 26

D-Tyr-Gly-Val-D-Ile-Thr-Arg-Ile-Arg-NHCH$_2$CH$_3$

The desired compound is prepared from the resin-bound peptide of Example 24 using the method of Example 5.

EXAMPLE 27

Ac-D-Tyr-Gly-Val-D-Ile-Thr-Arg-Ile-Arg

The desired compound is prepared from the resin-bound peptide of Example 24 according to the method of Example 2.

EXAMPLE 28

Ac-D-Tyr-Gly-Val-D-Ile-Thr-Arg-Ile-Arg-NH$_2$

The desired compound is prepared from the resin-bound peptide of Example 25 according to the method of Example 2. MS (FAB) m/z 1018 (M+H)$^+$.

EXAMPLE 29

Ac-D-Tyr-Gly-Val-D-Ile-Thr-Arg-Ile-Arg-NHCH$_2$CH$_3$

The desired compound is prepared from the resin-bound Ac-D-Tyr-Gly-Val-D-Ile-Thr-Arg-Ile-Arg of Example 27 using the method of Example 5.

EXAMPLE 30

Gly-D-Val-Ile-D-Thr-D-Arg-D-Ile-D-Arg

The desired peptide is prepared according to the method of Example 3 except using 4-hydroxymethyl phenoxymethyl resin (Applied Biosystems) and coupling the amino acids to the resin in the following order using the conditions indicated.

| # Amino Acid | Coupling |
| --- | --- |
| 1. Fmoc-D-Arg(Pmc) | 30 minutes |
| 2. Fmoc-D-Ile | 30 minutes |
| 3. Fmoc-D-Arg(Pmc) | 30 minutes |
| 4. Fmoc-D-Thr(t-Bu) | 30 minutes |
| 5. Fmoc-Ile | 30 minutes |
| 6. Fmoc-D-Val | 30 minutes |
| 7. Fmoc-Gly | 30 minutes |

EXAMPLE 31

Gly-D-Val-Ile-D-Thr-D-Arg-D-Ile-D-Arg-NH$_2$

The desired compound is prepared according to the method of Example 3, by coupling the amino acids to the resin as described in Example 30.

EXAMPLE 32

Gly-D-Val-Ile-D-Thr-D-Arg-D-Ile-D-Arg-NHCH$_2$CH$_3$

The desired peptide is prepared from the resin bound peptide of Example 30 using the method of Example 5.

EXAMPLE 33

Ac-Gly-D-Val-Ile-D-Thr-D-Arg-D-Ile-D-Arg

The desired peptide is prepared from the resin bound peptide of Example 30 according to the method of Example 2.

EXAMPLE 34

Ac-Gly-D-Val-Ile-D-Thr-D-Arg-D-Ile-D-Arg-NH$_2$

The desired compound is prepared from the resin bound Gly-D-Val-Ile-D-Thr-D-Arg-D-Ile-D-Arg-NH$_2$ of Example 31 using the method of Example 2.

EXAMPLE 35

Ac-Gly-D-Val-Ile-D-Thr-D-Arg-D-Ile-D-Arg-NHCH$_2$CH$_3$

The desired compound is prepared from the resin bound Ac-Gly-D-Val-Ile-D-Thr-D-Arg-D-Ile-D-Arg of Example 33 using the method of Example 5. MS (FAB) m/e 855 (M+H)$^+$.

EXAMPLE 36

D-Arg-D-Ile-D-Arg-D-Thr-Ile-D-Val-Gly

The desired peptide is prepared according to the method of Example 1 using a Gly peptide synthesis column and coupling the amino acids to the resin in the following order using the conditions indicated.

| # Amino Acid | Coupling |
| --- | --- |
| 1. Fmoc-D-Val | 30 minutes |
| 2. Fmoc-Ile | 30 minutes |
| 3. Fmoc-D-Thr(t-Bu) | 30 minutes |
| 4. Fmoc-D-Arg(Pmc) | 30 minutes |
| 5. Fmoc-D-Ile | 30 minutes |
| 6. Fmoc-D-Arg(Pmc) | 30 minutes |

EXAMPLE 37

D-Arg-D-Ile-D-Arg-D-Thr-Ile-D-Val-Gly-NH$_2$

The desired compound is prepared according to the method of Example 3, by coupling the amino acids to the resin in the following order using the conditions indicated.

| # Amino Acid | Coupling |
| --- | --- |
| 1. Gly | 30 minutes |
| 2. Fmoc-D-Val | 30 minutes |
| 3. Fmoc-Ile | 30 minutes |
| 4. Fmoc-D-Thr(t-Bu) | 30 minutes |
| 5. Fmoc-D-Arg(Pmc) | 30 minutes |
| 6. Fmoc-D-Ile | 30 minutes |
| 7. Fmoc-D-Arg(Pmc) | 30 minutes |

EXAMPLE 38

D-Arg-D-Ile-D-Arg-D-Thr-Ile-D-Val-Gly-NHCH$_2$CH$_3$

The desired peptide is prepared from the resin bound peptide of Example 36 using the method of Example 5.

EXAMPLE 39

Ac-D-Arg-D-Ile-D-Arg-D-Thr-Ile-D-Val-Gly

The desired peptide is prepared from the resin bound peptide of Example 36 according to the method of Example 2.

EXAMPLE 40

Ac-D-Arg-D-Ile-D-Arg-D-Thr-Ile-D-Val-Gly-NH$_2$

The desired compound is prepared from the resin bound D-Arg-D-Ile-D-Arg-D-Thr-Ile-D-Val-Gly-NH$_2$ of Example 37 using the method of Example 2.

EXAMPLE 41

Ac-D-Arg-D-Ile-D-Arg-D-Thr-Ile-D-Val-Gly-NHCH$_2$CH$_3$

The desired compound is prepared from the resin bound Ac-D-Arg-D-Ile-D-Arg-D-Thr-Ile-D-Val-Gly of Example 36 using the method of Example 5. MS (FAB) m/e 855 (M+H)$^+$.

EXAMPLE 42

Gly-Val-D-Ile-Lys-Arg-Ile-Arg

The desired compound is prepared according to the method of Example 1 by coupling the amino acids to the resin in the following order using the conditions indicated.

| # Amino Acid | Coupling |
|---|---|
| 1. Fmoc-Ile | 30 minutes |
| 2. Fmoc-Arg(Pmc) | 30 minutes |
| 3. Fmoc-Lys(Boc) | 30 minutes |
| 4. Fmoc-D-Ile | 30 minutes |
| 5. Fmoc-Val | 30 minutes |
| 6. Fmoc-Gly | 30 minutes |

EXAMPLE 43

Ac-Gly-Val-D-Ile-Lys-Arg-Ile-Arg

The desired compound is prepared according to the method of Example 2, except using the resin-bound peptide prepared as in Example 42.

EXAMPLE 44

Gly-Val-D-Ile-Lys-Arg-Ile-Arg-NH$_2$

The desired compound is prepared according to the method of Example 3, by coupling the amino acids to the resin in the following order using the conditions indicated.

| # Amino Acid | Coupling |
|---|---|
| 1. Fmoc-Arg(Pmc) | 30 minutes |
| 2. Fmoc-Ile | 30 minutes |
| 3. Fmoc-Arg(Pmc) | 30 minutes |
| 4. Fmoc-Lys(Boc) | 30 minutes |
| 5. Fmoc-D-Ile | 30 minutes |
| 6. Fmoc-Val | 30 minutes |
| 7. Fmoc-Gly | 30 minutes |

EXAMPLE 45

Ac-Gly-Val-D-Ile-Lys-Arg-Ile-Arg-NH$_2$

The desired compound is prepared according to the method of Example 2, except using the resin-bound peptide prepared as in Example 44.

EXAMPLE 46

Gly-Val-D-Ile-Lys-Arg-Ile-Arg-NHCH$_2$CH$_3$

The desired peptide is prepared according to the method of Example 5, except substituting the resin-bound peptide of Example 42 for the resin-bound peptide of Example 1.

EXAMPLE 47

Ac-Gly-Val-D-Ile-Lys-Arg-Ile-Arg-NHCH$_2$CH$_3$

The desired compound is prepared from the resin-bound Ac-Gly-Val-D-Ile-Lys-Arg-Ile-Arg of Example 43 using the method of Example 5.

EXAMPLE 48

Gly-Val-D-Ile-Lys-Arg-Ser-Arg

The desired compound is prepared according to the method of Example 1 by coupling the amino acids to the resin in the following order using the conditions indicated.

| # Amino Acid | Coupling |
|---|---|
| 1. Fmoc-Ser(tBu) | 30 minutes |
| 2. Fmoc-Arg(Pmc) | 30 minutes |
| 3. Fmoc-Lys(Boc) | 30 minutes |
| 4. Fmoc-D-Ile | 30 minutes |
| 5. Fmoc-Val | 30 minutes |
| 6. Fmoc-Gly | 30 minutes |

EXAMPLE 49

Ac-Gly-Val-D-Ile-Lys-Arg-Ser-Arg

The desired compound is prepared according to the method of Example 2, except using the resin-bound peptide prepared as in Example 48.

EXAMPLE 50

Gly-Val-D-Ile-Lys-Arg-Ser-Arg-NH$_2$

The desired compound is prepared according to the method of Example 3, by coupling the amino acids to the resin in the following order using the conditions indicated.

| # Amino Acid | Coupling |
|---|---|
| 1. Fmoc-Arg(Pmc) | 30 minutes |
| 2. Fmoc-Ser(tBu) | 30 minutes |
| 3. Fmoc-Arg(Pmc) | 30 minutes |
| 4. Fmoc-Lys(Boc) | 30 minutes |
| 5. Fmoc-D-Ile | 30 minutes |
| 6. Fmoc-Val | 30 minutes |
| 7. Fmoc-Gly | 30 minutes |

EXAMPLE 51

Ac-Gly-Val-D-Ile-Lys-Arg-Ser-Arg-NH$_2$

The desired compound is prepared according to the method of Example 2, except using the resin-bound peptide prepared as in Example 50.

EXAMPLE 52

Gly-Val-D-Ile-Lys-Arg-Ser-Arg-NHCH$_2$CH$_3$

The desired peptide is prepared according to the method of Example 5, except substituting the resin-bound peptide of Example 48 for the resin-bound peptide of Example 1.

EXAMPLE 53

Ac-Gly-Val-D-Ile-Lys-Arg-Ser-Arg-NHCH$_2$CH$_3$

The desired compound is prepared from the resin-bound Ac-Gly-Val-D-Ile-Lys-Arg-Ser-Arg of Example 49 using the method of Example 5.

EXAMPLE 54

Gly-Val-D-Ile-Thr-Arg-Ser-Arg

The desired compound is prepared according to the method of Example 1 by coupling the amino acids to the resin in the following order using the conditions indicated.

| # | Amino Acid | Coupling |
|---|---|---|
| 1. | Fmoc-Ser(tBu) | 30 minutes |
| 2. | Fmoc-Arg(Pmc) | 30 minutes |
| 3. | Fmoc-Thr(t-Bu) | 30 minutes |
| 4. | Fmoc-D-Ile | 30 minutes |
| 5. | Fmoc-Val | 30 minutes |
| 6. | Fmoc-Gly | 30 minutes |

EXAMPLE 55

Ac-Gly-Val-D-Ile-Thr-Arg-Ser-Arg

The desired compound is prepared according to the method of Example 2, except using the resin-bound peptide prepared as in Example 54.

EXAMPLE 56

Gly-Val-D-Ile-Thr-Arg-Ser-Arg-NH$_2$

The desired compound is prepared according to the method of Example 3, by coupling the amino acids to the resin in the following order using the conditions indicated.

| # | Amino Acid | Coupling |
|---|---|---|
| 1. | Fmoc-Arg(Pmc) | 30 minutes |
| 2. | Fmoc-Ser(tBu) | 30 minutes |
| 3. | Fmoc-Arg(Pmc) | 30 minutes |
| 4. | Fmoc-Thr(t-Bu) | 30 minutes |
| 5. | Fmoc-D-Ile | 30 minutes |
| 6. | Fmoc-Val | 30 minutes |
| 7. | Fmoc-Gly | 30 minutes |

EXAMPLE 57

Ac-Gly-Val-D-Ile-Thr-Arg-Ser-Arg-NH$_2$

The desired compound is prepared according to the method of Example 2, except using the resin-bound peptide prepared as in Example 56.

EXAMPLE 58

Gly-Val-D-Ile-Thr-Arg-Ser-Arg-NHCH$_2$CH$_3$

The desired peptide is prepared according to the method of Example 5, except substituting the resin-bound peptide of Example 54 for the resin-bound peptide of Example 1.

EXAMPLE 59

Ac-Gly-Val-D-Ile-Thr-Arg-Ser-Arg-NHCH$_2$CH$_3$

The desired compound is prepared from the resin-bound Ac-Gly-Val-D-Ile-Thr-Arg-Ser-Arg of Example 55 using the method of Example 5.

EXAMPLE 60

Gly-Val-D-Ile-Tyr-Arg-Ile-Arg

The desired compound is prepared according to the method of Example 1 by coupling the amino acids to the resin in the following order using the conditions indicated.

| # | Amino Acid | Coupling |
|---|---|---|
| 1. | Fmoc-Ile | 30 minutes |
| 2. | Fmoc-Arg(Pmc) | 30 minutes |
| 3. | Fmoc-Tyr(t-Bu) | 30 minutes |
| 4. | Fmoc-D-Ile | 30 minutes |
| 5. | Fmoc-Val | 30 minutes |
| 6. | Fmoc-Gly | 30 minutes |

EXAMPLE 61

Ac-Gly-Val-D-Ile-Tyr-Arg-Ile-Arg

The desired compound is prepared according to the method of Example 2, except using the resin-bound peptide prepared as in Example 60.

EXAMPLE 62

Gly-Val-D-Ile-Tyr-Arg-Ile-Arg-NH$_2$

The desired compound is prepared according to the method of Example 3, by coupling the amino acids to the resin in the following order using the conditions indicated.

| # | Amino Acid | Coupling |
|---|---|---|
| 1. | Fmoc-Arg(Pmc) | 30 minutes |
| 2. | Fmoc-Ile | 30 minutes |
| 3. | Fmoc-Arg(Pmc) | 30 minutes |
| 4. | Fmoc-Tyr(t-Bu) | 30 minutes |
| 5. | Fmoc-D-Ile | 30 minutes |
| 6. | Fmoc-Val | 30 minutes |
| 7. | Fmoc-Gly | 30 minutes |

EXAMPLE 63

Ac-Gly-Val-D-Ile-Tyr-Arg-Ile-Arg-NH$_2$

The desired compound is prepared according to the method of Example 2, except using the resin-bound peptide prepared as in Example 62.

EXAMPLE 64

Gly-Val-D-Ile-Tyr-Arg-Ile-Arg-NHCH$_2$CH$_3$

The desired peptide is prepared according to the method of Example 5, except substituting the resin-bound peptide of Example 60 for the resin-bound peptide of Example 1.

EXAMPLE 65

Ac-Gly-Val-D-Ile-Tyr-Arg-Ile-Arg-NHCH$_2$CH$_3$

The desired compound is prepared from the resin-bound Ac-Gly-Val-D-Ile-Tyr-Arg-Ile-Arg of Example 61 using the method of Example 5.

EXAMPLE 66

Gly-Val-D-Ile-Tyr-Arg-Asn-Arg

The desired compound is prepared according to the method of Example 1 by coupling the amino acids to the resin in the following order using the conditions indicated.

| # Amino Acid | Coupling |
| --- | --- |
| 1. Fmoc-Asn(Trt) | 30 minutes |
| 2. Fmoc-Arg(Pmc) | 30 minutes |
| 3. Fmoc-Tyr(t-Bu) | 30 minutes |
| 4. Fmoc-D-Ile | 30 minutes |
| 5. Fmoc-Val | 30 minutes |
| 6. Fmoc-Gly | 30 minutes |

EXAMPLE 67

Ac-Gly-Val-D-Ile-Tyr-Arg-Asn-Arg

The desired compound is prepared according to the method of Example 2, except using the resin-bound peptide prepared as in Example 66.

EXAMPLE 68

Gly-Val-D-Ile-Tyr-Arg-Asn-Arg-NH$_2$

The desired compound is prepared according to the method of Example 3, by coupling the amino acids to the resin in the following order using the conditions indicated.

| # Amino Acid | Coupling |
| --- | --- |
| 1. Fmoc-Arg(Pmc) | 30 minutes |
| 2. Fmoc-Asn(Trt) | 30 minutes |
| 3. Fmoc-Arg(Pmc) | 30 minutes |
| 4. Fmoc-Tyr(t-Bu) | 30 minutes |
| 5. Fmoc-D-Ile | 30 minutes |
| 6. Fmoc-Val | 30 minutes |
| 7. Fmoc-Gly | 30 minutes |

EXAMPLE 69

Ac-Gly-Val-D-Ile-Tyr-Arg-Asn-Arg-NH$_2$

The desired compound is prepared according to the method of Example 2, except using the resin-bound peptide prepared as in Example 68.

EXAMPLE 70

Gly-Val-D-Ile-Tyr-Arg-Asn-Arg-NHCH$_2$CH$_3$

The desired peptide is prepared according to the method of Example 5, except substituting the resin-bound peptide of Example 66 for the resin-bound peptide of Example 1.

EXAMPLE 71

Ac-Gly-Val-D-Ile-Tyr-Arg-Asn-Arg-NHCH$_2$CH$_3$

The desired compound is prepared from the resin-bound Ac-Gly-Val-D-Ile-Tyr-Arg-Asn-Arg of Example 67 using the method of Example 5.

EXAMPLE 72

Gly-Val-D-Ile-Thr-Arg-Asn-Arg

The desired compound is prepared according to the method of Example 1 by coupling the amino acids to the resin in the following order using the conditions indicated.

| # Amino Acid | Coupling |
| --- | --- |
| 1. Fmoc-Asn(Trt) | 30 minutes |
| 2. Fmoc-Arg(Pmc) | 30 minutes |
| 3. Fmoc-Thr(t-Bu) | 30 minutes |
| 4. Fmoc-D-Ile | 30 minutes |
| 5. Fmoc-Val | 30 minutes |
| 6. Fmoc-Gly | 30 minutes |

EXAMPLE 73

Ac-Gly-Val-D-Ile-Thr-Arg-Asn-Arg

The desired compound is prepared according to the method of Example 2, except using the resin-bound peptide prepared as in Example 72.

EXAMPLE 74

Gly-Val-D-Ile-Thr-Arg-Asn-Arg-NH$_2$

The desired compound is prepared according to the method of Example 3, by coupling the amino acids to the resin in the following order using the conditions indicated.

| # Amino Acid | Coupling |
| --- | --- |
| 1. Fmoc-Arg(Pmc) | 30 minutes |
| 2. Fmoc-Asn(Trt) | 30 minutes |
| 3. Fmoc-Arg(Pmc) | 30 minutes |
| 4. Fmoc-Thr(t-Bu) | 30 minutes |
| 5. Fmoc-D-Ile | 30 minutes |
| 6. Fmoc-Val | 30 minutes |
| 7. Fmoc-Gly | 30 minutes |

EXAMPLE 75

Ac-Gly-Val-D-Ile-Thr-Arg-Asn-Arg-NH$_2$

The desired compound is prepared according to the method of Example 2, except using the resin-bound peptide prepared as in Example 74.

EXAMPLE 76

Gly-Val-D-Ile-Thr-Arg-Asn-Arg-NHCH$_2$CH$_3$

The desired peptide is prepared according to the method of Example 5, except substituting the resin-bound peptide of Example 72 for the resin-bound peptide of Example 1.

EXAMPLE 77

Ac-Gly-Val-D-Ile-Thr-Arg-Asn-Arg-NHCH$_2$CH$_3$

The desired compound is prepared from the resin-bound Ac-Gly-Val-D-Ile-Thr-Arg-Asn-Arg of Example 73 using the method of Example 5.

EXAMPLE 78

Ser-Pro-Trp-Ser-D-Ser-Ala-Ser-Val-Thr-Ala-Gly-Asp-Gly-Val-Ile-Thr-Arg-Ile-Arg

The desired compound is prepared according to the method of Example 1 and coupling the amino acids to the resin in the following order using the conditions indicated.

| # Amino Acid | Coupling |
| --- | --- |
| 1. Fmoc-Ile | 30 minutes |
| 2. Fmoc-Arg(Pmc) | 30 minutes |
| 3. Fmoc-Thr(t-Bu) | 30 minutes |
| 4. Fmoc-Ile | 30 minutes |
| 5. Fmoc-Val | 30 minutes |
| 6. Fmoc-Gly | 30 minutes |
| 7. Fmoc-Asp(O-tBu) | 30 minutes |
| 8. Fmoc-Gly | 30 minutes |
| 9. Fmoc-Ala | 30 minutes |
| 10. Fmoc-Thr(t-Bu) | 30 minutes |
| 11. Fmoc-Val | 30 minutes |
| 12. Fmoc-Ser(tBu) | 30 minutes |
| 13. Fmoc-Ala | 30 minutes |
| 14. Fmoc-D-Ser(tBu) | 30 minutes |
| 15. Fmoc-Ser(tBu) | 30 minutes |
| 16. Fmoc-Trp | 30 minutes |
| 17. Fmoc-Pro | 30 minutes |
| 18. Fmoc-Ser(tBu) | 30 minutes |

EXAMPLE 79

Ser-Pro-Trp-Ser-D-Ser-Ala-Ser-Val-Thr-Ala-Gly-Asp-Gly-Val-D-Ile-Thr-Arg-Ile-Arg

The desired compound is prepared according to the method of Example 1 and coupling the amino acids to the resin in the following order using the conditions indicated.

| # Amino Acid | Coupling |
| --- | --- |
| 1. Fmoc-Ile | 30 minutes |
| 2. Fmoc-Arg(Pmc) | 30 minutes |
| 3. Fmoc-Thr(t-Bu) | 30 minutes |
| 4. Fmoc-D-Ile | 30 minutes |
| 5. Fmoc-Val | 30 minutes |
| 6. Fmoc-Gly | 30 minutes |
| 7. Fmoc-Asp(OtBu) | 30 minutes |
| 8. Fmoc-Gly | 30 minutes |
| 9. Fmoc-Ala | 30 minutes |
| 10. Fmoc-Thr(t-Bu) | 30 minutes |
| 11. Fmoc-Val | 30 minutes |
| 12. Fmoc-Ser(tBu) | 30 minutes |
| 13. Fmoc-Ala | 30 minutes |
| 14. Fmoc-D-Ser(tBu) | 30 minutes |
| 15. Fmoc-Ser(tBu) | 30 minutes |
| 16. Fmoc-Trp | 30 minutes |
| 17. Fmoc-Pro | 30 minutes |
| 18. Fmoc-Ser(tBu) | 30 minutes |

EXAMPLE 80

Ser-Pro-Trp-D-Ser-Ser-Ala-Ser-Val-Thr-Ala-Gly-Asp-Gly-Val-D-Ile-Thr-Arg-Ile-Arg

The desired compound was prepared according to the method of Example 79 but substituting Fmoc-D-Ser(tBu) for amino acid number 15 and substituting Fmoc-Ser(tBu) for amino acid number 14.

What is claimed is:

1. A peptide or pharmaceutically acceptable salt thereof selected from the group consisting of T-Gly-Val-D-Ile-Thr-Arg-Ile-U, V-Gly-D-Val-Ile-D-Thr-D-Arg-D-Ile-W, X-D-Arg-D-Ile-D-Arg-D-Thr-Ile-D-Val-Y, and Z-Gly-Val-Ile-Thr-Arg-Ile-U wherein T is absent or is selected from
  a N-protecting group and
  a polypeptide of up to 12 amino acid residues optionally terminated with a N-protecting group;
U is selected from Arg and Arg-NR$^1$R$^2$
  wherein R$^1$ and R$^2$ are independently selected from hydrogen and alkyl of one to four carbon atoms;
V is absent or a N-protecting group;
W is selected from D-Arg and D-Arg-NR$^1$R$^2$;
X is absent or a N-protecting group;
Y is selected from Gly and Gly-NR$^1$R$^2$; and
Z is 1–12 amino acid residues optionally terminated with
  a N-protecting group
  wherein at least one of the amino acid residues is a D-amino acid residue.

2. A peptide or pharmaceutically acceptable salt thereof as defined by claim 1 of formula T-Gly-Val-D-Ile-Thr-Arg-Ile-U.

3. A peptide or pharmaceutically acceptable salt thereof as defined by claim 2 wherein U is selected from Arg and Arg-NHCH$_2$CH$_3$.

4. A peptide or pharmaceutically acceptable salt thereof as defined by claim 2 wherein T is absent.

5. A peptide or pharmaceutically acceptable salt thereof as defined by claim 2 wherein T is acetyl.

6. A peptide or pharmaceutically acceptable salt thereof as defined by claim 2 wherein T is a peptide of up to 12 amino acid residues optionally capped with acetyl.

7. A peptide or pharmaceutically acceptable salt thereof as defined by claim 6 wherein T is Ser-Pro-Trp-Ser-Ser-Ala-Ser-Val-Thr-Ala-Gly-Asp- optionally terminated with acetyl.

8. A peptide or pharmaceutically acceptable salt thereof as defined by claim 6 wherein T is Gly-Asp- optionally terminated with acetyl.

9. A peptide or pharmaceutically acceptable salt thereof as defined by claim 2 selected from the group consisting of
  Gly-Val-D-Ile-Thr-Arg-Ile-Arg,
  Gly-Val-D-Ile-Thr-Arg-Ile-Arg-NH$_2$,
  Gly-Val-D-Ile-Thr-Arg-Ile-Arg-NHCH$_2$CH$_3$,
  Ac-Gly-Val-D-Ile-Thr-Arg-Ile-Arg,
  Ac-Gly-Val-D-Ile-Thr-Arg-Ile-Arg-NH$_2$,
  Ac-Gly-Val-D-Ile-Thr-Arg-Ile-Arg-NHCH$_2$CH$_3$,
  Tyr-Gly-Val-D-Ile-Thr-Arg-Ile-Arg,
  Tyr-Gly-Val-D-Ile-Thr-Arg-Ile-Arg-NH$_2$,
  Tyr-Gly-Val-D-Ile-Thr-Arg-Ile-Arg-NHCH$_2$CH$_3$,
  Ac-Tyr-Gly-Val-D-Ile-Thr-Arg-Ile-Arg,
  Ac-Tyr-Gly-Val-D-Ile-Thr-Arg-Ile-Arg-NH$_2$,
  Ac-Tyr-Gly-Val-D-Ile-Thr-Arg-Ile-Arg-NHCH$_2$CH$_3$,
  D-Tyr-Gly-Val-D-Ile-Thr-Arg-Ile-Arg,
  D-Tyr-Gly-Val-D-Ile-Thr-Arg-Ile-Arg-NH$_2$,
  D-Tyr-Gly-Val-D-Ile-Thr-Arg-Ile-Arg-NHCH$_2$CH$_3$,
  Ac-D-Tyr-Gly-Val-D-Ile-Thr-Arg-Ile-Arg,
  Ac-D-Tyr-Gly-Val-D-Ile-Thr-Arg-Ile-Arg-NH$_2$,
  Ac-D-Tyr-Gly-Val-D-Ile-Thr-Arg-Ile-Arg-NHCH$_2$CH$_3$,
  Gly-Asp-Gly-Val-D-Ile-Thr-Arg-Ile-Arg,
  Gly-Asp-Gly-Val-D-Ile-Thr-Arg-Ile-Arg-NH$_2$,
  Gly-Asp-Gly-Val-D-Ile-Thr-Arg-Ile-Arg-NNHCH$_2$CH$_3$,
  Ac-Gly-Asp-Gly-Val-D-Ile-Thr-Arg-Ile-Arg,
  Ac-Gly-Asp-Gly-Val-D-Ile-Thr-Arg-Ile-Arg-NH$_2$, Ac-Gly-Asp-Gly-Val-D-Ile-Thr-Arg-Ile-Arg-NHCH$_2$CH$_3$, Ser-Pro-Trp-Ser-Ser-Ala-Ser-Val-Thr-Ala-Gly-Asp-Gly-Val-D-Ile-Thr-Arg-Ile-Arg, Ser-Pro-Trp-Ser-Ser-Ala-Ser-Val-Thr-Ala-Gly-Asp-Gly-Val-D-Ile-Thr-Arg-Ile-Arg-NH$_2$, Ser-Pro-Trp-Ser-Ser-Ala-Ser-Val-Thr-Ala-Gly-Asp-Gly-Val-D-Ile-Thr-Arg-Ile-Arg-NHCH$_2$CH$_3$, Ac-Ser-Pro-Trp-Ser-Ser-Ala-Ser-Val-Thr-Ala-Gly-Asp-Gly-Val-D-Ile-Thr-Arg-Ile-Arg, Ac-Ser-Pro-Trp-Ser-Ser-Ala-Ser-Val-Thr-Ala-Gly-Asp-Gly-Val-D-Ile-Thr-Arg-Ile-Arg-NH$_2$ and Ac-Ser-Pro-Trp-Ser-Ser-Ala-Ser-Val-Thr-Ala-Gly-Asp-Gly-Val-D-Ile-Thr-Arg-Ile-Arg-NHCH$_2$CH$_3$.

10. A peptide or pharmaceutically acceptable salt thereof according to claim 1 having the formula V-Gly-D-Val-Ile-D-Thr-D-Arg-D-Ile-W.

11. A peptide or pharmaceutically acceptable salt thereof as defined by claim 10 wherein W is selected from D-Arg and D-Arg-NHCH$_2$CH$_3$.

12. A peptide or pharmaceutically acceptable salt thereof as defined by claim 11 wherein V is absent.

13. A peptide or pharmaceutically acceptable salt thereof as defined by claim 11 wherein V is acetyl.

14. A peptide or pharmaceutically acceptable salt thereof as defined by claim 10 selected from the group consisting of Gly-D-Val-Ile-D-Thr-D-Arg-D-Ile-D-Arg, Gly-D-Val-Ile-D-Thr-D-Arg-D-Ile-D-Arg-NH$_2$, Gly-D-Val-Ile-D-Thr-D-Arg-D-Ile-D-Arg-NHCH$_2$CH$_3$, Ac-Gly-D-Val-Ile-D-Thr-D-Arg-D-Ile-D-Arg, Ac-Gly-D-Val-Ile-D-Thr-D-Arg-D-Ile-D-Arg-NH$_2$ and Ac-Gly-D-Val-Ile-D-Thr-D-Arg-D-Ile-D-Arg-NHCH$_2$CH$_3$.

15. A peptide or pharmaceutically acceptable salt thereof as defined by claim I having the formula X-D-Arg-D-Ile-D-Arg-D-Thr-Ile-D-Val-Y.

16. A peptide or pharmaceutically acceptable salt thereof as defined by claim 15 wherein Y is selected from Gly and Gly-NHCH$_2$CH$_3$.

17. A peptide or pharmaceutically acceptable salt thereof as defined by claim 16 wherein X is absent.

18. A peptide or pharmaceutically acceptable salt thereof as defined by claim 16 wherein X is acetyl.

19. A peptide or pharmaceutically acceptable salt thereof as defined by claim 15 selected from the group consisting of D-Arg-D-Ile-D-Arg-D-Thr-Ile-D-Val-Gly, D-Arg-D-Ile-D-Arg-D-Thr-Ile-D-Val-Gly-NH$_2$, D-Arg-D-Ile-D-Arg-D-Thr-Ile-D-Val-Gly-NHCH$_2$CH$_3$, Ac-D-Arg-D-Ile-D-Arg-D-Thr-Ile-D-Val-Gly, Ac-D-Arg-D-Ile-D-Arg-D-Thr-Ile-D-Val-Gly-NH$_2$ and Ac-D-Arg-D-Ile-D-Arg-D-Thr-Ile-D-Val-Gly-NHCH$_2$CH$_3$.

20. A composition for treating a patient in need of anti-angiogenesis therapy comprising the peptide of claim 1 in combination with a pharmaceutically acceptable carrier.

21. A method of treating a patient in need of anti-angiogenesis therapy comprising administering to the patient a therapeutically effective amount of the peptide of claim 1.

22. A composition for the treatment of a disease selected from the group consisting of cancer, arthritis, psoriasis, angiogenesis in the eye associated with infection or surgical intervention, macular degeneration and diabetic retinopathy comprising the peptide of claim 1 in combination with a pharmaceutically acceptable carrier.

23. A method of treating a disease selected from the group consisting of cancer, arthritis, psoriasis, angiogenesis in the eye associated with infection or surgical intervention, macular degeneration and diabetic retinopathy comprising administering to the patient a therapeutically effective amount of the peptide of claim 1.

24. A method of isolating the TSP-1 receptor from endothelial cells comprising binding a peptide according to claim 1 to the receptor, isolating the peptide receptor complex and purifying the receptor.

25. A peptide or pharmaceutically acceptable salt thereof as defined by claim 6 wherein T is Ser-Pro-Trp-Ser-D-Ser-Ala-Ser-Val-Thr-Ala-Gly-Asp- optionally terminated with acetyl.

26. A peptide or pharmaceutically acceptable salt thereof as defined by claim 2 selected from the group consisting of Ser-Pro-Trp-Ser-D-Ser-Ala-Ser-Val-Thr-Ala-Gly-Asp-Gly-Val-D-Ile-Thr-Arg-Ile-Arg, Ser-Pro-Trp-Ser-D-Ser-Ala-Ser-Val-Thr-Ala-Gly-Asp-Gly-Val-D-Ile-Thr-Arg-Ile-Arg-NH$_2$, Ser-Pro-Trp-Ser-D-Ser-Ala-Ser-Val-Thr-Ala-Gly-Asp-Gly-Val-D-Ile-Thr-Arg-Ile-Arg-NHCH$_2$CH$_3$, Ac-Ser-Pro-Trp-Ser-D-Ser-Ala-Ser-Val-Thr-Ala-Gly-Asp-Gly-Val-D-Ile-Thr-Arg-Ile-Arg, Ac-Ser-Pro-Trp-Ser-D-Ser-Ala-Ser-Val-Thr-Ala-Gly-Asp-Gly-Val-D-Ile-Thr-Arg-Ile-Arg-NH$_2$, and Ac-Ser-Pro-Trp-Ser-D-Ser-Ala-Ser-Val-Thr-Ala-Gly-Asp-Gly-Val-D-Ile-Thr-Arg-Ile-Arg-NHCH$_2$CH$_3$.

27. A peptide or pharmaceutically acceptable salt thereof as defined by claim 1 of formula Z-Gly-Val-Ile-Thr-Arg-Ile-U.

28. A peptide or pharmaceutically acceptable salt thereof as defined by claim 27 wherein U is selected from Arg, Arg-NH$_2$, and Arg-NHCH$_2$CH$_3$ and Z is optionally terminated with an N-protecting group.

29. A peptide or pharmaceutically acceptable salt thereof as defined by claim 27 wherein Z is 1–12 amino acid residues optionally terminated with an N-protecting group and at least one of the amino acids is a D-amino acid.

30. A peptide or pharmaceutically acceptable salt thereof as defined by claim 29 wherein Z is Ser-Pro-Trp-Ser-D-Ser-Ala-Ser-Val-Thr-Ala-Gly-Asp- optionally terminated with acetyl.

31. A peptide or pharmaceutically acceptable salt thereof as defined by claim 27 selected from the group consisting of Ser-Pro-Trp-Ser-D-Ser-Ala-Ser-Val-Thr-Ala-Gly-Asp-Gly-Val-Ile-Thr-Arg-Ile-Arg, Ser-Pro-Trp-Ser-D-Ser-Ala-Ser-Val-Thr-Ala-Gly-Asp-Gly-Val-Ile-Thr-Arg-Ile-Arg-NH$_2$, Ser-Pro-Trp-Ser-D-Ser-Ala-Ser-Val-Thr-Ala-Gly-Asp-Gly-Val-Ile-Thr-Arg-Ile-Arg-NHCH$_2$CH$_3$, Ac-Ser-Pro-Trp-Ser-D-Ser-Ala-Ser-Val-Thr-Ala-Gly-Asp-Gly-Val-Ile-Thr-Arg-Ile-Arg, Ac-Ser-Pro-Trp-Ser-D-Ser-Ala-Ser-Val-Thr-Ala-Gly-Asp-Gly-Val-Ile-Thr-Arg-Ile-Arg-NH$_2$, and Ac-Ser-Pro-Trp- Ser-D-Ser-Ala-Ser-Val-Thr-Ala-Gly-Asp-Gly-Val-Ile-Thr-Arg-Ile-Arg-NHCH$_2$CH$_3$.

32. A peptide or pharmaceutically acceptable salt thereof as defined by claim 29 wherein Z is Ser-Pro-Trp-D-Ser-Ser-Ala-Ser-Val-Thr-Ala-Gly-Asp- optionally terminated with acetyl.

33. A peptide or pharmaceutically acceptable salt thereof as defined by claim 27 selected from the group consisting of Ser-Pro-Trp-D-Ser-Ser-Ala-Ser-Val-Thr-Ala-Gly-Asp-Gly-Val-Ile-Thr-Arg-Ile-Arg,
Ser-Pro-Trp-D-Ser-Ser-Ala-Ser-Val-Thr-Ala-Gly-Asp-Gly-Val-Ile-Thr-Arg-Ile-Arg-NH$_2$,
Ser-Pro-Trp-D-Ser-Ser-Ala-Ser-Val-Thr-Ala-Gly-Asp-Gly-Val-Ile-Thr-Arg-Ile-Arg-NHCH$_2$CH$_3$,
Ac-Ser-Pro-Trp-D-Ser-Ser-Ala-Ser-Val-Thr-Ala-Gly-Asp-Gly-Val-Ile-Thr-Arg-Ile-Arg,
Ac-Ser-Pro-Trp-D-Ser-Ser-Ala-Ser-Val-Thr-Ala-Gly-Asp-Gly-Val-Ile-Thr-Arg-Ile-Arg-NH$_2$, and
Ac-Ser-Pro-Trp-D-Ser-Ser-Ala-Ser-Val-Thr-Ala-Gly-Asp-Gly-Val-Ile-Thr-Arg-Ile-Arg-NHCH$_2$CH$_3$.

34. A compound or pharmaceutically acceptable salt thereof selected from the group consisting of Gly-Val-D-Ile-Thr-Arg-Ile-Arg,
Gly-Val-D-Ile-Thr-Arg-Ile-Arg-NH$_2$,
Gly-Val-D-Ile-Thr-Arg-Ile-Arg-NHCH$_2$CH$_3$,
Ac-Gly-Val-D-Ile-Thr-Arg-Ile-Arg,
Ac-Gly-Val-D-Ile-Thr-Arg-Ile-Arg-NH$_2$,
Ac-Gly-Val-D-Ile-Thr-Arg-Ile-Arg-NHCH$_2$CH$_3$,
Tyr-Gly-Val-D-Ile-Thr-Arg-Ile-Arg,
Tyr-Gly-Val-D-Ile-Thr-Arg-Ile-Arg-NH$_2$,
Tyr-Gly-Val-D-Ile-Thr-Arg-Ile-Arg-NHCH$_2$CH$_3$,
Ac-Tyr-Gly-Val-D-Ile-Thr-Arg-Ile-Arg,
Ac-Tyr-Gly-Val-D-Ile-Thr-Arg-Ile-Arg-NH$_2$,
Ac-Tyr-Gly-Val-D-Ile-Thr-Arg-Ile-Arg-NHCH$_2$CH$_3$,
D-Tyr-Gly-Val-D-Ile-Thr-Arg-Ile-Arg,
D-Tyr-Gly-Val-D-Ile-Thr-Arg-Ile-Arg-NH$_2$,
D-Tyr-Gly-Val-D-Ile-Thr-Arg-Ile-Arg-NHCH$_2$CH$_3$,
Ac-D-Tyr-Gly-Val-D-Ile-Thr-Arg-Ile-Arg,
Ac-D-Tyr-Gly-Val-D-Ile-Thr-Arg-Ile-Arg-NH$_2$,
Ac-D-Tyr-Gly-Val-D-Ile-Thr-Arg-Ile-Arg-NHCH$_2$CH$_3$,
Gly-Asp-Gly-Val-D-Ile-Thr-Arg-Ile-Arg,
Gly-Asp-Gly-Val-D-Ile-Thr-Arg-Ile-Arg-NH$_2$,
Gly-Asp-Gly-Val-D-Ile-Thr-Arg-Ile-Arg-NHCH$_2$CH$_3$,
Ac-Gly-Asp-Gly-Val-D-Ile-Thr-Arg-Ile-Arg,
Ac-Gly-Asp-Gly-Val-D-Ile-Thr-Arg-Ile-Arg-NH$_2$,
Ac-Gly-Asp-Gly-Val-D-Ile-Thr-Arg-Ile-Arg-NHCH$_2$CH$_3$,
Ser-Pro-Trp-Ser-Ser-Ala-Ser-Val-Thr-Ala-Gly-Asp-Gly-Val-D-Ile-Thr-Arg-Ile-Arg,
Ser-Pro-Trp-Ser-Ser-Ala-Ser-Val-Thr-Ala-Gly-Asp-Gly-Val-D-Ile-Thr-Arg-Ile-Arg-NH$_2$,
Ser-Pro-Trp-Ser-Ser-Ala-Ser-Val-Thr-Ala-Gly-Asp-Gly-Val-D-Ile-Thr-Arg-Ile-Arg-NHCH$_2$CH$_3$,
Ac-Ser-Pro-Trp-Ser-Ser-Ala-Ser-Val-Thr-Ala-Gly-Asp-Gly-Val-D-Ile-Thr-Arg-Ile-Arg,
Ac-Ser-Pro-Trp-Ser-Ser-Ala-Ser-Val-Thr-Ala-Gly-Asp-Gly-Val-D-Ile-Thr-Arg-Ile-Arg-NH$_2$,
Ac-Ser-Pro-Trp-Ser-Ser-Ala-Ser-Val-Thr-Ala-Gly-Asp-Gly-Val-D-Ile-Thr-Arg-Ile-Arg-NHCH$_2$CH$_3$,
Gly-D-Val-Ile-D-Thr-D-Arg-D-Ile-D-Arg,
Gly-D-Val-Ile-D-Thr-D-Arg-D-Ile-D-Arg-NH$_2$,
Gly-D-Val-Ile-D-Thr-D-Arg-D-Ile-D-Arg-NHCH$_2$CH$_3$,
Ac-Gly-D-Val-Ile-D-Thr-D-Arg-D-Ile-D-Arg,
Ac-Gly-D-Val-Ile-D-Thr-D-Arg-D-Ile-D-Arg-NH$_2$,
Ac-Gly-D-Val-Ile-D-Thr-D-Arg-D-Ile-D-Arg-NHCH$_2$CH$_3$,
D-Arg-D-Ile-D-Arg-D-Thr-Ile-D-Val-Gly,
D-Arg-D-Ile-D-Arg-D-Thr-Ile-D-Val-Gly-NH$_2$,
D-Arg-D-Ile-D-Arg-D-Thr-Ile-D-Val-Gly-NHCH$_2$CH$_3$,
Ac-D-Arg-D-Ile-D-Arg-D-Thr-Ile-D-Val-Gly,
Ac-D-Arg-D-Ile-D-Arg-D-Thr-Ile-D-Val-Gly-NH$_2$,
Ac-D-Arg-D-Ile-D-Arg-D-Thr-Ile-D-Val-Gly-NHCH$_2$CH$_3$,
Gly-Val-D-Ile-Lys-Arg-Ile-Arg,
Ac-Gly-Val-D-Ile-Lys-Arg-Ile-Arg,
Gly-Val-D-Ile-Lys-Arg-Ile-Arg-NH$_2$,
Ac-Gly-Val-D-Ile-Lys-Arg-Ile-Arg-NH$_2$,
Gly-Val-D-Ile-Lys-Arg-Ile-Arg-NHCH$_2$CH$_3$,
Ac-Gly-Val-D-Ile-Lys-Arg-Ile-Arg-NHCH$_2$CH$_3$,
Gly-Val-D-Ile-Lys-Arg-Ser-Arg,
Ac-Gly-Val-D-Ile-Lys-Arg-Ser-Arg,
Gly-Val-D-Ile-Lys-Arg-Ser-Arg-NH$_2$,
Ac-Gly-Val-D-Ile-Lys-Arg-Ser-Arg-NH$_2$,
Gly-Val-D-Ile-Lys-Arg-Ser-Arg-NHCH$_2$CH$_3$,
Ac-Gly-Val-D-Ile-Lys-Arg-Ser-Arg-NHCH$_2$CH$_3$,
Gly-Val-D-Ile-Thr-Arg-Ser-Arg,
Ac-Gly-Val-D-Ile-Thr-Arg-Ser-Arg,
Gly-Val-D-Ile-Thr-Arg-Ser-Arg-NH$_2$,
Ac-Gly-Val-D-Ile-Thr-Arg-Ser-Arg-NH$_2$,
Gly-Val-D-Ile-Thr-Arg-Ser-Arg-NHCH$_2$CH$_3$,
Ac-Gly-Val-D-Ile-Thr-Arg-Ser-Arg-NHCH$_2$CH$_3$,
Gly-Val-D-Ile-Tyr-Arg-Ile-Arg,
Ac-Gly-Val-D-Ile-Tyr-Arg-Ile-Arg,
Gly-Val-D-Ile-Tyr-Arg-Ile-Arg-NH$_2$,
Ac-Gly-Val-D-Ile-Tyr-Arg-Ile-Arg-NH$_2$,
Gly-Val-D-Ile-Tyr-Arg-Ile-Arg-NHCH$_2$CH$_3$,
Ac-Gly-Val-D-Ile-Tyr-Arg-Ile-Arg-NHCH$_2$CH$_3$,
Gly-Val-D-Ile-Tyr-Arg-Asn-Arg,
Ac-Gly-Val-D-Ile-Tyr-Arg-Asn-Arg,
Gly-Val-D-Ile-Tyr-Arg-Asn-Arg-NH$_2$,
Ac-Gly-Val-D-Ile-Tyr-Arg-Asn-Arg-NH$_2$,
Gly-Val-D-Ile-Tyr-Arg-Asn-Arg-NHCH$_2$CH$_3$,
Ac-Gly-Val-D-Ile-Tyr-Arg-Asn-Arg-NHCH$_2$CH$_3$,
Gly-Val-D-Ile-Thr-Arg-Asn-Arg,
Ac-Gly-Val-D-Ile-Thr-Arg-Asn-Arg,
Gly-Val-D-Ile-Thr-Arg-Asn-Arg-NH$_2$,
Ac-Gly-Val-D-Ile-Thr-Arg-Asn-Arg-NH$_2$,
Gly-Val-D-Ile-Thr-Arg-Asn-Arg-NHCH$_2$CH$_3$,
Ac-Gly-Val-D-Ile-Thr-Arg-Asn-Arg-NHCH$_2$CH$_3$,
Ser-Pro-Trp-Ser-D-Ser-Ala-Ser-Val-Thr-Ala-Gly-Asp-Gly-Val-D-Ile-Thr-Arg-Ile-Arg,
Ser-Pro-Trp-Ser-D-Ser-Ala-Ser-Val-Thr-Ala-Gly-Asp-Gly-Val-D-Ile-Thr-Arg-Ile-Arg-NH$_2$,
Ser-Pro-Trp-Ser-D-Ser-Ala-Ser-Val-Thr-Ala-Gly-Asp-Gly-Val-D-Ile-Thr-Arg-Ile-Arg-NHCH$_2$CH$_3$,
Ac-Ser-Pro-Trp-Ser-D-Ser-Ala-Ser-Val-Thr-Ala-Gly-Asp-Gly-Val-D-Ile-Thr-Arg-Ile-Arg,
Ac-Ser-Pro-Trp-Ser-D-Ser-Ala-Ser-Val-Thr-Ala-Gly-Asp-Gly-Val-D-Ile-Thr-Arg-Ile-Arg-NH$_2$, and
Ac-Ser-Pro-Trp-Ser-D-Ser-Ala-Ser-Val-Thr-Ala-Gly-Asp-Gly-Val-D-Ile-Thr-Arg-Ile-Arg-NHCH$_2$CH$_3$,
Ser-Pro-Trp-Ser-D-Ser-Ala-Ser-Val-Thr-Ala-Gly-Asp-Gly-Val-Ile-Thr-Arg-Ile-Arg,
Ser-Pro-Trp-Ser-D-Ser-Ala-Ser-Val-Thr-Ala-Gly-Asp-Gly-Val-Ile-Thr-Arg-Ile-Arg-NH$_2$, Ser-Pro-Trp-Ser-D-Ser-Ala-Ser-Val-Thr-Ala-Gly-Asp-Gly-Val-Ile-Thr-Arg-Ile-Arg-NHCH$_2$CH$_3$, Ac-Ser-Pro-Trp-Ser-D-Ser-Ala-Ser-Val-Thr-Ala-Gly-Asp-Gly-Val-Ile-Thr-Arg-Ile-Arg, Ac-Ser-Pro-Trp-Ser-D-Ser-Ala-Ser-Val-Thr-Ala-Gly-Asp-Gly-Val-Ile-Thr-Arg-Ile-Arg-NH$_2$, Ac-Ser-Pro-Trp-Ser-D-Ser-Ala-Ser-Val-Thr-Ala-Gly-Asp-Gly-Val-Ile-Thr-Arg-Ile-Arg-NHCH$_2$CH$_3$, Ser-Pro-Trp-D-Ser-Ser-Ala-Ser-Val-Thr-Ala-Gly-Asp-Gly-Val-Ile-Thr-Arg-Ile-Arg, Ser-Pro-Trp-D-Ser-Ser-Ala-Ser-Val-Thr-Ala-Gly-Asp-Gly-Val-Ile-Thr-Arg-Ile-Arg-NH$_2$, Ser-Pro-Trp-D-Ser-Ser-Ala-Ser-Val-Thr-Ala-Gly-Asp-Gly-Val-Ile-Thr-Arg-Ile-Arg-NHCH$_2$CH$_3$, Ac-Ser-Pro-Trp-D-Ser-Ser-Ala-Ser-Val-Thr-Ala-Gly-Asp-Gly-Val-Ile-Thr-Arg-Ile-Arg, Ac-Ser-Pro-Trp-D-Ser-Ser-Ala-Ser-Val-Thr-Ala-Gly-Asp-Gly-Val-Ile-Thr-Arg-Ile-Arg-NH$_2$, and Ac-Ser-Pro-Trp-D-Ser-Ser-Ala-Ser-Val-Thr-Ala-Gly-Asp-Gly-Val-Ile-Thr-Arg-Ile-Arg-NHCH$_2$CH$_3$.

* * * * *

UNITED STATES PATENT AND TRADEMARK OFFICE
CERTIFICATE OF CORRECTION

PATENT NO. : 5,932,545
DATED : August 3, 1999
INVENTOR(S) : Jack Henkin et al.

It is certified that error appears in the above-identified patent and that said Letters Patent is hereby corrected as shown below:

Column 1, before the Technical Field please insert the following paragraph: Government License Rights: The U.S. Government has a paid-up license in this invention and the right in limited circumstances to require the patent owner to license others on reasonable terms as provided for by the terms of Grant No. CA52750 awarded by the National Institutes of Health Column 16, Line 13, after Biosystems, please insert - - Foster City, CA - -

Column 16, Line 23, after "between" please delete 100 and insert - -10°C- -

Signed and Sealed this

Twenty-sixth Day of September, 2000

Attest:

Q. TODD DICKINSON

*Attesting Officer*      *Director of Patents and Trademarks*

UNITED STATES PATENT AND TRADEMARK OFFICE
CERTIFICATE OF CORRECTION

PATENT NO. : 5,932,545
DATED : August 3, 1999
INVENTOR(S) : Jack Henkin et al.

It is certified that error appears in the above-identified patent and that said Letters Patent is hereby corrected as shown below:

<u>Title Page,</u>
Section [73], please add Northwestern University,
Evanston, Illinois as co-assignee Signed and Sealed this Thirty-first Day of July, 2001

*Attest:*

*Nicholas P. Godici*

*Attesting Officer*

NICHOLAS P. GODICI
*Acting Director of the United States Patent and Trademark Office*